(12) United States Patent
Slepian et al.

(10) Patent No.: US 10,413,901 B2
(45) Date of Patent: Sep. 17, 2019

(54) METHODS, DEVICES, AND SYSTEMS FOR MICROFLUIDIC STRESS EMULATION

(71) Applicants: ARIZONA BOARD OF REGENTS ON BEHALF OF THE UNIVERSITY OF ARIZONA, Tucson, AZ (US); THE RESEARCH FOUNDATION FOR THE STATE UNIVERSITY OF NEW YORK, Albany, NY (US); POLITECNICO DI MILANO, Milan (IT)

(72) Inventors: Marvin J. Slepian, Tucson, AZ (US); Alberto C. Redaelli, Milan (IT); Marco Rasponi, Milan (IT); Danny Bluestein, Albany, NY (US)

(73) Assignees: ARIZONA BOARD OF REGENTS ON BEHALF OF THE UNIVERSITY OF ARIZONA, Tucson, AZ (US); THE RESEARCH FOUNDATION FOR THE STATE UNIVERSITY OF NEW YORK, Albany, NY (US); POLITECNICO DI MILANO, Milan (IT)

(*) Notice: Subject to any disclaimer, the term of this patent is extended or adjusted under 35 U.S.C. 154(b) by 0 days.

(21) Appl. No.: 15/507,616

(22) PCT Filed: Aug. 28, 2015

(86) PCT No.: PCT/US2015/047421
§ 371 (c)(1),
(2) Date: Feb. 28, 2017

(87) PCT Pub. No.: WO2016/033455
PCT Pub. Date: Mar. 3, 2016

(65) Prior Publication Data
US 2017/0246632 A1    Aug. 31, 2017

Related U.S. Application Data

(60) Provisional application No. 62/043,977, filed on Aug. 29, 2014.

(51) Int. Cl.
*B01L 3/00* (2006.01)
*G01N 33/50* (2006.01)
(Continued)

(52) U.S. Cl.
CPC .... *B01L 3/502746* (2013.01); *G01N 15/1056* (2013.01); *G01N 33/5091* (2013.01);
(Continued)

(58) Field of Classification Search
None
See application file for complete search history.

(56) References Cited

U.S. PATENT DOCUMENTS

| | | |
|---|---|---|
| 5,256,538 A | 10/1993 | Aiken et al. |
| 5,457,028 A | 10/1995 | Amrani |

(Continued)

FOREIGN PATENT DOCUMENTS

| | | |
|---|---|---|
| WO | 2001/005948 | 1/2001 |
| WO | 2012/024194 | 2/2012 |
| WO | 2013/153541 | 10/2013 |

OTHER PUBLICATIONS

Alemu and Bluestein "Flow-induced platelet activation and damage accumulation in a mechanical heart valve: numerical studies." 2007 Artif Organs. 31(9):677-88.
(Continued)

*Primary Examiner* — Xiaoyun R Xu
(74) *Attorney, Agent, or Firm* — Casimir Jones, S.C.; Tanya A. Arenson

(57) ABSTRACT

Provided herein is technology relating to microfluidic devices and particularly, but not exclusively, to devices, (Continued)

methods, systems, and kits for imparting stresses on a fluid flowing through a microfluidic device that is designed to mimic a stress profile of a macrofluidic device or pathology.

6 Claims, 9 Drawing Sheets

(51) Int. Cl.
G01N 15/10 (2006.01)
G01N 33/569 (2006.01)
A61B 5/145 (2006.01)

(52) U.S. Cl.
CPC ..... A61B 5/14546 (2013.01); B01L 2400/086 (2013.01); G01N 33/56966 (2013.01); G01N 33/56972 (2013.01); G01N 2015/1006 (2013.01); G01N 2800/224 (2013.01); G01N 2800/226 (2013.01)

(56) References Cited

U.S. PATENT DOCUMENTS

| | | |
|---|---|---|
| 2004/0131500 A1 | 7/2004 | Chow |
| 2005/0261543 A1 | 11/2005 | Abe et al. |
| 2007/0060605 A1 | 3/2007 | Flaumenhaft |
| 2012/0058500 A1 | 3/2012 | Mitchell et al. |
| 2012/0330629 A1 | 12/2012 | Prabhakarpandian et al. |
| 2014/0244184 A1 | 8/2014 | Lynn et al. |

OTHER PUBLICATIONS

Alemu et al. "Design optimization of a mechanical heart valve for reducing valve thrombogenicity—A case study with ATS valve." 2010 ASAIO J. 56:389-396.
Anderson, et al., "Simultaneous fluorescence-activated cell sorter analysis of two distinct transcriptional elements within a single cell using engineered green fluorescent proteins" Proc. Natl. Acad. Sci. USA 93:8508-8511(1996).
Apel et al. "Assessment of Hemolysis Related Quantities in a Microaxial Blood Pump by Computational Fluid Dynamics" 2001 Artif. Organs 25(5):341-347.
Ballyk and colleagues "Simulation of non-Newtonian blood flow in an end-to-side anastomosis." (1994) Biorheology 31(5):565-586.
Bauer J., "Advances in cell separation: Recent developments in counterflow centrifugal elutriation and continuous low cell separation." J. Chromatog. B, 722:55-69 (1999).
Berman et al., "Measurement of Anti-PADGEM Antibodies" Methods in Enzymology 169:314, 1989.
Chien et al. "Effects of hematocrit and plasma proteins on human blood rheology at low shear rates." 1966 J. Appl. Physiol. 21:81-87.
Chiu, G. Girdhar, M. Xenos, Y. Alemu, J. S. Soares, S. Einav, M. Slepian, and D. Bluestein, "Thromboresistance comparison of the HeartMateII Ventricular Assist Device With the Device Thrombogenicity Emulation-Optimized HeartAssist 5 VAD," Journal of Biomechanical Engineering, vol. 136, pp. 021014, 2014.
Eckman, and J. Ranjit, "Bleeding and thrombosis in patients with continuous-flow ventricular assist devices." Circulation 125:3038-3047 (2012).
Ferziger and Peric, Computational Methods for Fluid Dynamics, Springer (1999), 11 pages, TOC only.
Friend and L. Yeo. "Fabrication of microfluidic devices using polydimethylsiloxane," Biomicrofluidics, vol. 4, pp. 026502, 2010.

Girdhar et al (2012) "Device thrombogenicity emulation: a novel method for optimizing mechanical circulatory support device thromboresistance," PLoS One 7(3): e32463, 2012.
Girdhar et al. "Biological Effects of Dynamic Shear Stress in Cardiovascular Pathologies and Devices" 2012 Expert Rev. Med. Devices, 5(2):167-181.
International Search Report and Written Opinion, International Patent Application No. PCT/US2015/047421, dated Jan. 8, 2016.
Jesty and Bluestein "Acetylated prothrombin as a substrate in the measurement of the procoagulant activity of platelets: Elimination of the feedback activation of platelets by thrombin. Anal Biochem." 1999 Biochem. 272:64-70.
Lundgren (1969). "Model equation for nonhomogeneous turbulence" Physics of Fluids A 12 (3): 485-497.
Mani et al. "Point-Of-Care Coagulation Testing for Assessment of the Pharmacodynamic Anticoagulant Effect of Direct Oral Anticoagulant" 2014 Ther. Drug Monit. 36(5):624-631.
Mehra, G. C. Stewart, P. A. Uber, "The vexing problem of thrombosis in long-term mechanical circulatory support." J Heart Lung Transpl. 33:1-11 (2014).
Moore, et at., "Lymphocyte Fractionation Using Immunomagnetic Colloid and a Dipole Magnet Flow Cell Sorter" J. Biochem. Biophys. Methods 37:11-33 (1998).
Morsi and Alexander "An investigation of particle trajectories in two-phase flow systems" 1972 J. Fluid Mech. 55 (2):193-208.
Nobili, M., Sheriff, J., Morbiducci, U., Redaelli, A., & Bluestein, D. "Platelet activation due to hemodynamic shear stresses: damage accumulation model and comparison to in vitro measurements." ASAIO Journal, 54(1), pp. 64-72, 2008.
Pelosi et al. (2014) "Computational evaluation of the thrombogenic potential of a hollow-fiber oxygenator with integrated heat exchanger during extracorporeal circulation" Biomechanics and Modeling in Mechanobiology 13(2): 349-361.
Pelosi, J. Sheriff, M. Stevanella, G.B. Fiore, D. Bluestein and A. Redaelli, "Computational evaluation of the thrombogenic potential of a hollow-fiber oxygenator with integrated heat exchanger during extracorporeal circulation," Biomechanics and Modeling in Mechanobiology, 10.1007/s10237-012-0445-0, 2013.
Quake and A. Scherer, "From Micro to Nano Fabrication with Soft Materials," Science, vol. 290, pp. 1536-1540, 2000.
Squires and Quake (2005), "Microfluidics: Fluid physics at the nanoliter scale". Reviews of Modern Physics 77: 977.
Starling, R. C., Moazami, N., Silvestry, S. C., Ewald, G., Rogers, J. G., Milano, C.et al. "Unexpected abrupt increase in left ventricular assist device thrombosis," The New England Journal of Medicine, 370(1), pp. 33-40, 2014.
Stewart, GC and Givetz MM, "Mechanical Circulatory Support for Advanced Heart Failure: Patients and Technology in Evolution," Circulation, vol. 125, pp. 1304-1315, 2012.
Unger "Monolithic microfabricated valves and pumps by multilayer soft lithography." (2000) Science 288:113-116.
Von Ruden, et al., "The Pharmacotherapy Implications of Ventricular Assist Device in the Patient With End-Stage Heart Failure" J. Pharm. Pract. 25(2):232:249 (2012).
Whitesides "Overview The origins and the future of microfluidics" 2006 Nature 442:368-373.
Kenos, G. Girdhar, Y. Alemu, J. Jesty, M. Slepian, Einav, S., Bluestein, D. "Device Thrombogenicity Emulator (DTE) Design optimization methodology for cardiovascular devices: A study in two bileaflet MHV designs," in JournalofBiomechanics, vol. 43, pp. 2400-2409, 2010.
Partial EP Search Report, EP Patent Application No. 15835910.9, dated Apr. 12, 2018, 13 pages.
Tsai, M. et al. "In vitro modeling of the microvascular occlusion and thrombosis that occur in hematologic diseases using microfluidic technology" Journal of Clinical Investigation, vol. 22, No. 1, Jan. 3, 2012, pp. 408-418.

METHODS, DEVICES, AND SYSTEMS FOR MICROFLUIDIC STRESS EMULATION

STATEMENT REGARDING FEDERALLY SPONSORED RESEARCH OR DEVELOPMENT

This invention was made with government support under Grant No. U01 EB012487, awarded by NIH. The government has certain rights in the invention.

FIELD

Provided herein is technology relating to microfluidic devices and particularly, but not exclusively, to devices, methods, systems, and kits for imparting stresses on a fluid flowing through a microfluidic device that is designed to mimic a stress profile of a macrofluidic device.

BACKGROUND

Thrombosis—and attendant significant morbidity and mortality—associated with the use of blood-contacting diagnostic and therapeutic devices (e.g., stents, ventricular assist devices (VADs), heart valves, the total artificial heart (TAH), etc.) significantly limits these technologies. In particular, thrombosis of ventricular assist devices is a significant complication compromising device efficacy with attendant risks of systemic embolization, stroke, pump stop and death. Presently, anti-thrombotic therapy is utilized to mitigate thrombotic risk. Drugs such as aspirin and dypridamole are largely dosed empirically without individualized testing of efficacy in a given patient. To date, testing systems available for examining anti-platelet agent efficacy are limited in that they are largely central lab-based and typically examine drug efficacy under conditions that do not represent the flow and shear conditions of the patient during actual VAD use. Thus, a technology for individualized point-of-care monitoring of patient thrombogenic risk, under the dynamic flow and shear conditions actually existent in vivo would improve patient care and safety.

SUMMARY

Mechanical circulatory support (MCS) devices have emerged in recent years as significant, effective, therapeutic systems providing restoration of hemodynamics for patients with progressive, advanced, and end-stage heart failure (see, e.g., Stewart, G C and Givetz M M, "Mechanical Circulatory Support for Advanced Heart Failure: Patients and Technology in Evolution," Circulation, vol. 125, pp. 1304-1315, 2012). However, use of MCS devices has been impaired by device-associated thrombosis, which can reduce or stop device function and cause recurrent heart failure, systemic emboli, possible stroke, and death in patients. Device-associated thrombosis in patients has been particularly associated with ventricular assist devices (VAD) such as the HEARTMATE II device (see, e.g., Starling, R. C., Moazami, N., Silvestry, S. C., Ewald, G., Rogers, J. G., Milano, C. et al. "Unexpected abrupt increase in left ventricular assist device thrombosis," The New England Journal of Medicine, 370(1), pp. 33-40, 2014).

Presently, device-associated thrombosis is mitigated by administering anti-thrombotic agents (e.g. aspirin, dipyridamole) to all VAD patients. While anti-thrombotic agents can be effective in mitigating biochemical or inflammatory activation of platelets, they are largely ineffective for shear stress-induced platelet activation. In addition, these agents are administered largely empirically without "personalization" of the regimen for a specific patient or specific device. While previous studies have attempted to measure the efficacy of anti-thrombotic therapy on an individual basis, the only systems available for the measurements were large, laboratory-based apparatuses that are not amenable to rapid (e.g., at least daily) bedside use (e.g., a light-based aggregometry apparatus or a platelet function analyzer such as a PFA-100). Further, existing technologies largely operate under static conditions or with minimal blood agitation and thus do not examine anti-thrombotic drug efficacy under actual blood flow and shear conditions associated with a given VAD.

Experiments conducted during the course of developing embodiments for the present technology designed microfluidic platforms able to emulate representative shear stress profiles of mechanical circulatory support (MCS) devices. First, a range of microfluidic channels able to replicate representative shear stress patterns observed in MCS devices were designed. Second, the flexibility of microfluidic technology in generating dynamic shear stress profiles was explored by modulating the geometrical features of the channels. Finally, microfluidic channel systems able to emulate the shear stress profiles of two commercial VADs were designed. From CFD analyses, it was demonstrated that the VAD-emulating microfluidic systems were able to replicate the main characteristics of the shear stress waveforms of the macroscale VADs (i.e. shear stress peaks and duration). Such results establish the basis for a lab-on-chip POC system able to perform device-specific and patient-specific platelet activation state assays.

Accordingly, provided herein is technology related to a method for monitoring the thrombogenic state in a patient treated with a medical device, the method comprising modeling the shear stress profile of the medical device; reproducing the shear stress profile of the medical device in a microfluidic device; flowing a sample from the patient through the microfluidic device; and testing the thrombogenic potential of the sample to monitor the thrombogenic state of the patient. In some embodiments, the medical device is a mechanical circulatory support device. In some embodiments, the medical device is a ventricular assist device. Some embodiments further comprise separating platelets from a blood sample to provide the sample. In some embodiments, the testing comprises testing platelet activation state. In some embodiments, the modeling comprises device thrombogenicity emulation and/or producing a probability density function of the device. Further, in some embodiments the modeling comprising determining individual particle trajectories for particles flowing through the device. In yet other embodiments, the methods comprise adjusting the dose of a drug administered to the patient. In some embodiments, the drug is an anti-thrombosis drug administered to the patient. In some embodiments, the method evaluates the efficacy of a drug or exogenous agent in modulating defined shear profile-mediated (e.g., as characterized by a PDF) platelet or other blood cell activation.

In some embodiments, a sample is acquired for testing from the patient 1 to 10 times (e.g., 1, 2, 3, 4, 5, 6, 7, 8, 9, or 10 times) a day. In some embodiments the testing is repeated 1 to 10 times (e.g., 1, 2, 3, 4, 5, 6, 7, 8, 9, or 10 times) a day. In some embodiments, the sample has a volume of 1 to 100 nanoliters (e.g., 1, 5, 10, 20, 30, 40, 50, 60, 70, 80, 90, or 100 nl). In some embodiments the sample has a volume from 100 nanoliter to 1 milliliter.

Additional embodiments provide a microfluidic device for imparting shear stress on a fluid sample that reproduces the shear stress imparted on the fluid sample by a macrofluidic device. In some embodiments, the shear stress imparted on the fluid sample by the macrofluidic device is modeled using device thrombogenicity emulation. In some embodiments, the device comprises a microfluidic channel comprising narrow regions to impart shear stress on a sample flowing through the channel. In some embodiments, the device comprises a channel designed to impart shear stress on a sample according to a shear stress history probability density function describing the macrofluidic device.

Further embodiments comprise components such as, e.g., a cell separation component, an assay component, a platelet separating component, a platelet activation state assay component, a detector, a data storage component, a telemetry or other communication component, and/or a power/battery module, etc.

In some embodiments, the macrofluidic device is a mechanical circulatory support device. And, in some embodiments, the macrofluidic device is a ventricular assist device. In other embodiments, the macrofluidic device may be a stent, catheter, pump, valve, diagnostic sensor, therapeutic drug delivery device, or power module.

In other embodiments, the macrofluidic device may be in situ tissue of the individual or animal itself. For example, the macrofluidic element may be a stenosed coronary artery, a narrowed orifice of an atrial appendage, a dilated outpouching of an aortic aneurysm, or any other altered anatomical pathology that will lead to deranged shear in the blood stream.

In another aspect, the technology relates to embodiments of systems for imparting shear stress on a fluid sample comprising a macrofluidic device that imparts shear stress on a fluid; and a microfluidic device that reproduces the shear stress imparted on the fluid sample by the macrofluidic device. In some embodiments, the systems further comprise software to produce a model of a shear stress profile of the macrofluidic device. In some embodiments, the model is produced by device thrombogenicity emulation. In some embodiments, the model comprises a shear stress history probability density function describing the macrofluidic device.

Additional system embodiments provide a system for treating a patient having a cardiovascular disease, the system comprising defined internal pathology that contacts the cardiovascular system of the patient (e.g., a stenotic artery or dilated aneurysm or arterial flap or tear); and a microfluidic device that reproduces the shear stress imparted on blood by the pathology. In some embodiments the system comprises a macrofluidic device that contacts the cardiovascular system of the patient; and a microfluidic device that reproduces the shear stress imparted on blood by the macrofluidic device. In some embodiments, the system further comprises an anti-thrombotic drug. In some embodiments, the system further comprises software to produce a model of a shear stress profile of the pathology or macrofluidic device. In some embodiments, the system further comprises a component to test a sample from the patient after the sample flowed through the microfluidic device. In some embodiments, the system further comprises a component to indicate a drug dosage for administration to the patient. In some embodiments, the system further comprises software that accepts data from the component to test the sample and determines the drug dosage. And, in some embodiments, the component to test a sample performs a test of platelet activation state.

Additional method embodiments relate to a method for testing the effects of imparting shear stress on a fluid sample, the method comprising modeling a macrofluidic device or pathology that imparts shear stress on a fluid sample; producing a microfluidic device to reproduce the shear stress imparted on the fluid sample by a macrofluidic device or pathology; and testing a sample after it was flowed through the microfluidic device. In some embodiments, the modeling comprises producing a probability density function of the macrofluidic device or pathology. In some embodiments, the modeling comprises determining individual particle trajectories for particles flowing through the macrofluidic device or pathology.

Embodiments of method further provide a method for imparting shear stress on a fluid sample, the method comprising modeling a macrofluidic device or pathology that imparts shear stress on a fluid sample; producing a microfluidic device to reproduce the shear stress imparted on the fluid sample by a macrofluidic device or pathology; and flowing the fluid sample through the microfluidic device. In some embodiments, the modeling comprises producing a probability density function of the macrofluidic device or pathology. In some embodiments, the modeling comprises determining individual particle trajectories for particles flowing through the macrofluidic device or pathology.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1:
FIG. 1 is a schematic showing the top view of a microfluidic model of stress imparted by a HMII VAD.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "microfluidic device" refers to a device comprising fluidic structures and internal channels having microfluidic dimensions. These fluidic structures may include chambers, valves, vents, vias, pumps, inlets, nipples, and detection means, for example. Generally, microfluidic channels are fluid passages having at least one internal cross-sectional dimension that is less than approximately 500 μm to 1000 μm and typically between approximately 0.1 μm and approximately 500 μm. The microfluidic flow regime is characterized by "Poiseuille" or "laminar" flow (see, e.g., Staben et al. (2005) "Particle transport in Poiseuille flow in narrow channels" Intl J Multiphase Flow 31:529-47, and references cited therein).

As used herein, a "macrofluidic device" refers to a non-microfluidic device comprising at least one non-microfluidic feature (e.g., channel, chamber, etc.), that is, a feature that holds a non-microfluidic volume, e.g., at least 10 microliters, at least 20 microliters, at least 50 microliters, at least 100 microliters, at least 500 microliters, at least 1 ml, at least 10 ml, or at least 100 ml.

As used herein, the term "microfluidic channel" or "microchannel" refers to a fluid channel having variable length and one dimension in cross-section that is less than 500 to 1000 μm. Microfluidic fluid flow behavior in a microfluidic channel is highly non-ideal and laminar and may be more dependent on wall wetting properties, roughness, liquid viscosity, adhesion, and cohesion than on pressure drop from end to end or cross-sectional area. The microfluidic flow regime is often associated with the presence of "virtual liquid walls" in the channel. However, in larger channels, head pressures of 10 psi or more can generate transitional flow regimes bordering on turbulent flow, as can be important in rinse steps of assays.

As used herein, the term "microfluidic pump" includes, e.g., bulbs, bellows, diaphragms, or bubbles intended to force movement of fluids, where the substructures of the pump have a thicknesses or other dimension of less than 1 millimeter. Such pumps include the mechanically actuated recirculating pumps described in U.S. Pat. No. 6,743,399 and U.S. Pat. App. Pub. No. 2005/0106066. Such pumps may be robotically operated or operated by hand. Electroosmotic pumps are also provided. Such pumps can be used in place of external drives to propulse the flow of samples in microfluidic devices.

As used herein, the term "bellows pump" refers to a device formed as a cavity, often cylindrical in shape, bisected in coronal section by an elastomeric diaphragm to form a first and a second half-chamber that are not fluidically connected. The diaphragm is controlled by a pneumatic pulse generator connected to the first half-chamber. Positive pressure above the diaphragm distends it, displacing the contents of the second half-chamber, negative gauge pressure (suction) retracts it, expanding the second half chamber and drawing fluid in.

As used herein, the term "microfluidic valve" refers to a genus of hydraulic, mechanic, pneumatic, magnetic, and/or electrostatic actuator flow controllers with at least one dimension smaller than 500 to 1000 μm. A representative flap valve of the genus is described in U.S. Pat. No. 6,431,212. Also included are check valves. One class of valves refers to a configuration in which a flow channel and a control channel intersect and are separated by an elastomeric membrane that can be deflected into or retracted from the flow channel in response to an actuation force in the control channel. Patents describing species of microfluidic valves include U.S. Pat. Nos. 5,971,355; 6,418,968; 6,518,99; 6,620,273; 6,748,975; 6,767,194; 6,901,949; and U.S. Pat. Pub. Nos. 2002/0195152 and 2005/02005816.

As used herein, a "check valve" is a one-way valve.

As used herein, the term "self-priming" refers to a microfluidic channel that is fabricated from a material or is treated so that the channel is wettable and capillary flow begins generally without the need to prime the channel.

As used herein, the term "via" refers to a step in a microfluidic channel that provides a fluid pathway from one substrate layer to another substrate layer above or below, characteristic of laminated devices built from layers.

As used herein, the term "pillow" refers to an on-board reagent pack formed from a deformable sacculus, for example a mylar microbag, optionally enclosed in a pneumatically actuated device for puncturing to bag to release its contents at a controlled time. Co-laminates of a metal and a plastic are preferred for stability considerations.

As used herein, the term "blister pack" refers to an on-board reagent pack under a deformable (or elastic) diaphragm. In some embodiments, a blister pack is used to deliver reagents by pressurizing the diaphragm and may appose a "sharp", such as a metal chevron, so that pressure on the diaphragm ruptures the "pillow" (see pillow). These may be used with check valves or closable vents to produce directional fluid flow and reagent delivery. Elastic diaphragms are readily obtained, e.g., from polyurethane, polysilicone, polybutadiene, and nitrile (see "elastomer" below). Deformable, inelastic diaphragms are provided in some embodiments comprising polyethylene terephthalate (PET), mylar, polypropylene, polycarbonate, or nylon, for example. Other suitable materials for a deformable film include parafilm, latex, foil, and polyethylene terephthalate. Key factors in selecting a deformable film include the yield point and the deformation relaxation coefficient (elastic modulus).

Use of these devices permits delivery or acceptance of a fluid while isolating the contents of the microfluidic device from the external environment, and protecting the user from exposure to the fluid contents.

As used herein, the term "waste chamber" or "waste sequestration receptacle" and the like refers to a cavity or a chamber that serves as a receptacle for sequestering, e.g., a discharged sample, a rinse solution, waste reagents, etc. A waste chamber includes a wicking material (see wick) in some embodiments. Waste chambers may also be sealed under an elastic isolation membrane sealingly attached to the body of the microfluidic device. In some embodiments, this inner membrane expands as a bibulous material therein expands, thus enclosing the waste material. The cavity outside the isolation membrane is vented to atmosphere so that the waste material is contained and isolated. Waste chambers may optionally contain dried or liquid sterilants.

As used herein a "wick" refers to a bibulous material used to propulse fluid flow by capillary wetting in place of, or in concert with, microfluidic pumps. The bibulous core typically includes a fibrous web of natural or synthetic fibers, and also often includes certain absorbent gelling materials usually referred to as "hydrogels", "superabsorbent", or "hydrocolloid" materials. Materials include papers, sponges, diaper materials, Contec-Wipe, and others. Dessicants may also be used, such as calcium sulfate, calcium sulfate, silica gel, alone or in combination with bibulous materials.

As used herein, the term "trap" refers to a fluid trap (e.g., comprising a "dam") that isolates a waste reservoir from a vent.

As used herein a "vent" refers to a pore intercommunicating between an internal cavity and the atmosphere. In some embodiments, a vent comprises a filter element that is permeable to gas, but is hydrophobic and resists wetting. Optionally these filter elements have pore diameters of 0.45 micrometers or less. Filter elements of this type and construction may also be placed internally, for example to isolate a valve or bellows pump from the pneumatic manifold controlling it.

As used herein, the term "elastomer" refers to a material that deforms when force is applied to it and returns to its original shape when the force is removed. The elasticity exhibited by elastomeric materials can be characterized by a Young's modulus. Elastomeric materials utilized in the microfluidic devices disclosed herein typically have a Young's modulus of between approximately 1 Pa to approximately 1 TPa, in other instances between approximately 10 Pa to approximately 100 GPa, in still other instances between apprximately 20 Pa to approximately 1 GPa, in yet other instances between approximately 50 Pa to approximately 10 MPa, and in certain instances between approximately 100 Pa to approximately 1 MPa. Elastomeric materials having a Young's modulus outside of these ranges can also be utilized depending upon the needs of a particular application.

In some embodiments, a "deformable film", e.g., lacking elasticity is used in the microfluidic devices of the technology described.

As used herein, the term "conventional" designates that which is known in the prior art to which this technology relates.

As used herein, the term "means for a function" indicates that the scope of the technology encompasses all means for performing the function that are described herein and all other means commonly known in the art at the time of filing.

As used herein, the term "means for detecting" refers to an apparatus for displaying an endpoint, e.g., the result of an assay, and may include a detection channel and a means for evaluation of a detection endpoint. The assay may include detecting signals related to a physical shape change of platelets or other cellular elements flowing through the microfluidic device or macromolecular elements (e.g., von Willebrand factor). Alternatively the assay may involve a release reaction of an internal constituent, e.g. PF4, serotonin, or the like. The assay may involve expression of surface antigens or moieties detectable via various means— e.g., gpIIb/IIIa expression of p-selectin. The assay may involve an ELISA, e.g., for detection of the activated prothrombin complex (as described in Jesty & Bluestein (1999). "Acetylated prothrombin as a substrate in the measurement of the procoagulant activity of platelets: elimination of the feedback activation of platelets by thrombin" *Analytical Biochemistry* 272(1): 64-70, incorporated herein by reference in its entirety)

Detection endpoints are evaluated by an observer visually or by a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnetic particles, beads, and microspheres having color or impregnated with color or having a higher diffraction index may be used to facilitate visual or machine-enhanced detection of an assay endpoint. Magnifying lenses, optical filters, colored fluids, and labeling may be used to improve detection and interpretation of assay results. Means for detection may also include the use of "labels" or "tags" such as, but not limited to, dyes such as chromophores and fluorophores, radio frequency tags, plasmon resonance, spintronic, radiolabel, Raman scattering, chemoluminescence, or inductive moment as are known in the art. Fluorescence quenching detection endpoints are also included. A variety of substrate and product chromophores associated with enzyme-linked immunoassays are also well known in the art and provide a means for amplifying a detection signal so as to improve the sensitivity of the assay. In some embodiments, radionuclide detection systems are incorporated. Detection systems are optionally qualitative, quantitative, or semi-quantitative. Visual detection is preferred for its simplicity; however, detection means can involve visual detection, machine detection, manual detection, or automated detection.

As used herein, the terms "animal", "subject", and "patient" specifically include mammals, such as a human, as well as cattle, horses, dogs, cats, and birds, but also can include many other species having a cardiovascular system.

As used herein, a "therapeutic agent" is a drug, pharmaceutical, etc., and may be, e.g., an agent that changes viscosity or membrane properties of platelets. A therapeutic agent may be a nutraceutical or a food.

DETAILED DESCRIPTION

Mechanical circulatory support (MCS) devices have emerged as a major advance in the management of patients with advanced heart failure (G. C. Stewart, and M. M. Givetz, Circulation 125:1304-1315 (2012)). Despite their clinical success, MCS devices unfortunately are plagued by device-related thrombosis (M. R. Mehra, G. C. Stewart, P. A. Uber, J Heart Lung Transpl. 33:1-11 (2014)), often resulting in reduced function, recurrent heart failure, systemic emboli, stroke, pump stop and even death. To prevent thrombosis MCS-implanted patients rely on the use of a combination of anti-thrombotic agents (e.g. aspirin, dipyridamole, clopidrogel) to limit platelet activation resulting from passage through the device (P. M. Eckman, and J. Ranjit, Circulation 125:3038-3047 (2012); S. A. Von Ruden, et al., J. Pharm. Pract. 25(2):232:249 (2012)). Despite the use of these drugs, thrombosis has persisted as a clinical problem (Starling et al.

New Engl. J. Med. 370:33-40 (2014)). A weakness of the present pharmacologic strategy is the fact that administered drugs are typically monitored only in the peri-operative period, during hospitalization and immediately thereafter. Drug monitoring in the out-of-hospital home environment is still not a common practice, with few systems available for routine point-of-care or home-based monitoring of platelet function (Mani et al. 2014 Ther. Drug Monit. 36(5):624-631). More often, drug monitoring is performed with laboratory based devices, e.g. light-based aggregometry or PFA-100. These assays largely examine biochemical endpoints of platelet activation, studied under static conditions or constant shear flow, and are not reflective of the actual dynamic shear and flow that occurs in a given MCS device, particularly as to the shear stress levels and dose to which platelets are exposed.

Shear forces are a major means of activation of platelets, as platelets pass through small dimensions and unusual geometries at high speed in MCS systems. Many blood-contacting systems have been characterized, including MCS devices, and the overall shear stress history and dose as a probability density function (PDF) of a scalar value, termed Stress Accumulation (SA), that takes into account the shear stress levels and exposure time acting on individual platelets described. A PDF is device-specific and can be seen as its "thrombogenic footprint", representing a means of calculating the net shear exposure history of a large population of platelets passing through the device.

Device Thrombogenicity Emulation (DTE) as a methodology allows one to subject platelets to realistic shear stress profiles obtained from complex computational fluid dynamics (CFD) analyses performed within realistic geometries of cardiac devices (Xenos et al. 2010 J. Biomech. 43:2400-2409, Alemu et al. 2010 ASAIO J. 56:389-396). The flow path in the device is modeled and platelets are tracked in order to detect individual platelet trajectories that may drive them beyond the activation threshold. For this purpose, cumulative stress, i.e. the SA, is calculated along multiple flow trajectories (thousands of simulated platelet trajectories) and collapsed into PDFs. Extreme cases of platelet stress loading trajectories, termed as "hotspot" or "flight" trajectories, can be extracted from the PDF and reproduced in vitro for actual exposure of platelets via a novel lab system—a Hemodynamic Shearing Device (HSD) (Nobili et al. 2008 ASAIO J. 54(1):64-72). The HSD consists of a programmable high-torque servo motor-controller system (Baldor Electric Company, AR) that propels the platelet sample in a modified cone-Couette viscometer with the capability of exposing platelets to highly-controlled dynamic, uniform shear stress waveforms (Xenos et al. 2010 J. Biomech. 43:2400-2409). The HSD-treated platelet sample is then assayed for platelet activation via the Platelet Activation State (PAS) assay (Jesty and Bluestein 1999 Biochem. 272:64-70), which measures the rate of thrombin generation as a surrogate validated biomarker.

While initially developed to analyze mechanical heart valves (Xenos et al. 2010 J. Biomech. 43:2400-2409, Alemu et al. 2010 ASAIO J. 56:389-396), the DTE methodology has been utilized to evaluate and optimize MCS devices, such as ventricular assist devices (VADs) (Girdhar et al. 2012 Expert Rev. Med. Devices, 5(2):167-181). Herein, it was hypothesized that the individual shear and flow characteristics of a given VAD, i.e. defined hotspot trajectories, may be emulated in a microfluidic channel system. As such, creating a "Device-Specific" VAD microfluidic facsimile would ultimately allow development of a small, point-of-care, lab-on-a chip system that may be utilized readily at the bedside to assess the adequacy of anti-thrombotic drug efficacy. A point-of care system made of polydimethylsiloxane (PDMS), through standard soft lithography was envisioned (Whitesides 2006 Nature 442:368-373).

As such, the overall goal of the present study was to investigate the feasibility of designing microfluidic emulators capable of replicating MCS fluid dynamics in terms of dynamic shear stress history patterns. Here the PDFs of two VADs in actual clinical use were generated. Using these PDFs specific component shear stress peaks into fluid microchannel geometries were translated and replicated. The flexibility of this microfluidic approach was next examined via changing channel design features in order to modulate shear stress curves. Finally, two different microfluidic platforms were designed to emulate the shear stress history defined by the device specific PDFs of two commercial VADs.

Accordingly, provided herein is technology related to modeling the shear stress profile of platelets flowing through a device (e.g., a mechanical circulatory support device (MCS), a ventricular assist device (VAD), etc.) or a pathology (e.g. a stenotic artery, a dilated aenurysm, a vascular flap, a stenotic atrial appendage orifice) and utilizing the shear stress profile model to produce a microfluidic device that imparts a facsimile of the device or pathology shear stress profile on a fluid flowing through the microfluidic device. In some embodiments, the device-specific or pathology-specific microfluidic facsimile of the shear stress profile provides a point-of-care system for assessing blood flow and thrombogenic potential associated with an actual device or pathology in a patient. Further, in some embodiments the technology provides for assessing the efficacy of an anti-thrombotic agent under personalized conditions, thus reducing the likelihood of thrombosis and increasing overall patient safety.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Although the disclosure herein refers to certain illustrated embodiments, it is to be understood that these embodiments are presented by way of example and not by way of limitation. While the technology is described herein in relation to exemplary embodiments associated with blood flow and circulatory support devices, it is to be understood that the technology finds use in modeling shear stress in any fluid conduit (e.g., device, biological structure (e.g., vasculature), etc.) and producing a microfluidic model reproducing the shear stress profile of the fluid conduit for testing the effects of shear stress on a fluid.

Thrombogenicity Emulation

In some embodiments, the technology relates to "device thrombogenicity emulation" methods for characterizing, modeling, and/or predicting the shear stress and stress loading history of a fluid, e.g., blood, e.g., a population of blood particles (e.g., blood cells or platelets) exposed to flow through a given device (e.g., a MCS such as a VAD or total artificial heart (TAH)).

In particular, in some embodiments this technology ("thrombogenicity emulation") describes the stress, overall shear stress history, and dose as a probability density function (PDF). See, e.g., Girdhar et al (2012) "Device thrombogenicity emulation: a novel method for optimizing mechanical circulatory support device thromboresistance," PLoS One 7(3): e32463, 2012, incorporated herein by reference. PDFs may be generated from in silico modeling of the flow and fluid structure interactions obtained for the geometry of a device or of an internal pathology (e.g. an arterial stenosis), with dimensional data obtained from a variety of imaging modalities including angiography, CTA, MRI, MRA, intravascular ultrasound, or other clinically utilized modalities which can provide anatomic and geometric information for image reconstruction and calculation of a PDF and shear loading histories. Further, some embodiments characterize and model individual flight trajectories of particles (e.g., platelets), e.g., in a fluid (e.g., blood) flowing through a device (e.g., a MCS such as a VAD or TAH). Then, in some embodiments, the parameters of the model describing the flight trajectories are used to establish laboratory conditions for exposing actual platelets to shear stress in a laboratory system for studying the behavior of platelets and blood under the modeled stress conditions. In some embodiments, the laboratory system comprises use of a hemodynamic shearing device (HSD) to reproduce the modeled flight trajectories (see, e.g., Nobili, M., Sheriff, J., Morbiducci, U., Redaelli, A., & Bluestein, D. "Platelet activation due to hemodynamic shear stresses: damage accumulation model and comparison to in vitro measurements." ASAIO Journal, 54(1), pp. 64-72, 2008). In some exemplary experiments, this technology has been utilized to examine the shear stress activation threshold of platelets and to iterate and improve MCS design. Further, this methodology has been used in some embodiments to examine the efficacy of anti-thrombotic therapy for a given patient and a given MCS device.

In some embodiments, computational fluid dynamics (CFD) and in vitro experimental tests are used in combination to study shear-induced platelet activation by MCS devices (e.g., VAD or TAH) (see, e.g., Girdhar, G., Xenos, M., Alemu, Y., Lynch, B., Jesty, J., Einav, S., Slepian, M. J., Bluestein, D., "Device thrombogenicity emulation: a novel method for optimizing mechanical circulatory support device thromboresistance," PLoS One, vol. 7, issue 3, e32463, 2012). For example, in some embodiments CFD is used to extract shear stress parameters from modeled platelet trajectories within the device. Then, in some embodiments, subsequent experimental tests comprise use of a computer-controlled device, e.g., a hemodynamics-emulating device (e.g., a hemodynamic shearing device (HSD)) that comprises a programmable high-torque servo motor-controller system. The HSD drives the fluid in a cone-Couette viscometer setup to expose platelets to highly controlled dynamic shear stress patterns, e.g., based on the modeling of the device using CFD and/or thrombogenecity emulation. In some embodiments, platelet activity state (e.g., thrombogenic state or thrombogenic potential) after exposure to shear stress (e.g., via HSD or after flow through a device (e.g., a microfluidic device)) is detected using the platelet activity state (PAS) assay. In this way, the device thrombogenic potential is indirectly estimated without testing the actual device.

This technology finds use to evaluate the shear-induced platelet activation in biomedical devices such as mechanical heart valves, VADs, TAHs, and blood oxygenators (see, e.g., M. Xenos, G. Girdhar, Y. Alemu, J. Jesty, M. Slepian, Einav, S., Bluestein, D. "Device Thrombogenicity Emulator (DTE) Design optimization methodology for cardiovascular devices: A study in two bileaflet MHV designs," in Journal of Biomechanics, vol. 43, pp. 2400-09, 2010; W. Chiu, G. Girdhar, M. Xenos, Y. Alemu, J. S. Soares, S. Einav, M. Slepian, and D. Bluestein, "Thromboresistance comparison of the HeartMateII Ventricular Assist Device With the Device Thrombogenicity Emulation-Optimized HeartAssist 5 VAD," Journal of Biomechanical Engineering, vol. 136, pp. 021014, 2014; A. Pelosi, J. Sheriff, M. Stevanella, G. B. Fiore, D. Bluestein and A. Redaelli, "Computational evaluation of the thrombogenic potential of a hollow-fiber oxygenator with integrated heat exchanger during extracorporeal circulation," Biomechanics and Modeling in Mechanobiology, 10.1007/s10237-012-0445-0, 2013).

Reproducing Device Shear Stress in a Microfluidic Device

Embodiments of the technology relate to emulating the individual shear and flow characteristics (e.g., defined flight trajectories) of a given MCS device or a cardiovascular pathology in a microfluidic channel system. In particular, embodiments of the technology are related to a small point-of-care system comprising a "device specific" microfluidic facsimile for assessing anti-thrombotic drug activity in a patient. During the development of embodiments of the technology, experiments were conducted to test using microfluidic technologies to replicate the flow-related thrombogenic potential of MCSs. In particular, the geometry of microfluidic devices is designed to replicate a device-specific or pathology-specific shear stress curve based on the stress models previously determined for that device. Embodiments of the microfluidic devices provided herein provide advantages that expand the potential applications of this technology. For example, microfluidic tests require small samples (e.g., a small volume of blood), thus providing embodiments of methods for monitoring patient blood susceptibility and/or the effect of drug therapy frequently and on a routine basis.

Microfluidic Devices

Microfluidic technologies provide many advantages (see, e.g., S. R. Quake and A. Scherer, "From Micro to Nano Fabrication with Soft Materials," Science, vol. 290, pp. 1536-40, 2000). Generally, microfluidic devices handle small amounts of fluids, e.g., having volumes of 1-1000 μL, 1-1000 nL, 1-1000 pL, or 1-1000 fL. Microfluidic devices typically have a small size and consume small amounts of reagents and energy. Finally, advantages of the technology are related to the behavior of small volumes of fluids with the microstructures of a microfluidic device. See, e.g., Squires and Quake (2005), "Microfluidics: Fluid physics at the nanoliter scale". Reviews of Modern Physics 77: 977, incorporated herein by reference in its entirety.

For example, the microfluidic technologies described herein provide for testing a sample having a small volume (e.g., $10^{-9}$ to $10^{-18}$ liters), thus minimizing or eliminating patient discomfort (e.g., from acquiring blood samples having reduced volume) and reducing the quantities and related costs of reagents, compounds, and pharmaceuticals that are associated with clinical tests. Further, the high surface-to-volume ratio of microfluidic devices dramatically reduces reaction times. Moreover, microfluidic devices provide for precise fluid handling. And, finally, microfluidics allows one to manipulate and to run parallel tests on a single small device.

During the development of embodiments of the technology described herein, microfluidic platforms were designed to replicate the shear-related thrombogenic potential of MCSs, e.g., VADs as exemplified by a commercial VAD sold under the trade name HEARTMATE II® Left Ventricular Assist System (HMII) by Thoratec (Pleasanton, Calif.). Data collected during the experiments were compared to previous studies that used CFD to characterize platelet trajectories and shear stresses in the HMII (see, e.g., W. Chiu, G. Girdhar, M. Xenos, Y. Alemu, J. S. Soares, S. Einav, M. Slepian, and D. Bluestein, "Thromboresistance comparison of the HeartMateII Ventricular Assist Device With the Device Thrombogenicity Emulation-Optimized HeartAssist 5 VAD", Journal of Biomechanical Engineering, vol. 136, pp. 021014, 2014). In those studies, the shear stress loading waveforms were characterized by stress peaks ranging from 60 to 250 Pa over a time interval of 20 to 40 ms. In some embodiments, an "elevated" or "high" stress is a stress of greater than approximately 200 Pa.

During the development of embodiments of the technology provided herein, stress loading waveforms were used to design a microfluidic device comprising a channel having a series of stress-generating features (e.g., channel expansions and narrowings; see FIG. 1). The channels were designed to replicate the VAD shear stress profile, e.g., to subject blood samples flowing through the microfluidic device to specific shear stress trajectories characterized, for example, by the location (e.g., in time or space) of stress peaks, number of stress peaks, height (e.g., intensity) of stress peaks, and width (e.g., duration) of stress peaks. In some embodiments, the flow trajectories emulated stress profile "hot spots" within the VAD that generate the highest levels of platelet stress and thus the highest levels of platelet activation.

In some particular embodiments, the microfluidic device is characterized by a reference rectangular cross-section of 50 μm×25 μm (width×height). Microchannels are narrowed (e.g., by decreasing the width of the channel) to reduce the flow area and induce an increase in the shear stress levels experienced by the fluid (e.g., blood, e.g., blood comprising platelets). In some embodiments, features are sized to generate the desired shear stress peaks at a constant flow rate of 2 μl/minute of a fluid resembling whole blood. In some embodiments, physical design and production constraints limited microfluidic devices to have features larger than 5 μm and aspect ratios smaller than 20. In some embodiments, the geometry of the device was defined by analytical calculations and refined by means of CFD (see below).

In some embodiments a microfluidic device comprises multiple emulation channels repeated in series. In some embodiments a microfluidic device comprises multiple parallel emulation channels. Some embodiments increase the number of repetitions and amplify platelet activation using a plurality of (e.g., two, more than two) synchronized syringe pumps to flow the sample alternatively in the two directions.

During the development of embodiments of the technology provided herein, experiments were conducted to develop and test a microfluidic "facsimile" of the shear characteristics experienced in flow through a VAD. In particular embodiments, this model is used to develop a point-of-care system for examining anti-thrombotic drug efficacy of a given patient using a system representative of the flow and shear conditions that the patient is exposed to. The microfluidic technologies provide for controlling shear stress levels and generating different ranges of stresses within a single microfluidic device to mimic the stress histories of fluids flowing through the macroscale device. The microfluidic platform provides shear stresses up to 10,000 dyne/cm$^2$, which are not attainable with some existing technologies (e.g., HSD). Moreover, in some embodiments the microfluidic device comprises multiple parallel channels designed from different stress profiles to test multiple different shear stress histories simultaneously. For example, in some embodiments a standard 2-cm$^2$ microfabricated PDMS chip hosts tens (e.g., 1 to 100, e.g., approximately 10, 20, 30, 40, 50, 60, 70, 80, 90, or 100) of parallel microfluidic patterns to provide manifold parallel experiments or to test different shear stress history patterns simultaneously.

In some embodiments, the total pumping pressure is maintained at or below 10 atm. In some embodiments, a two-syringe pump system is used. In some embodiments, a single microchannel occupies approximately 0.5 mm$^2$ and tests a fluid sample of approximately 10 nanoliters.

In some embodiments, the microfluidic device comprises components to process a sample prior to delivery to the microfluidic emulation channel (e.g., a cell separator, a platelet separator) and in some embodiments the microfluidic device comprises components to process as sample after flow through the microfluidic emulation channel (e.g., a component to perform a platelet activation assay (PAS) and a component to detect a signal from the PAS, e.g., a detection means).

In some embodiments, blood is separated into components. See, e.g., Bauer, J. Chromatog. B, 722:55-69 (1999); Anderson, et al., Proc. Natl. Acad. Sci. USA 93:8508-8511 (1996); Moore, et at., J. Biochem. Biophys. Methods 37:1-2 (1998), incorporated herein by reference. See also PCT/US2011/047654.

In some embodiments, the microfluidic device comprises channels, chambers, or other reservoirs or vestibules, either with direct fluid communication and/or contact or with controlled contact (e.g., via gates, valves, or the like) to allow entry of a fluid or multiple fluids or reagents into the flow path (e.g., following upstream shear exposure) to create a mixing reaction allowing detection of the impact of shear. For example, some embodiments relate to flowing in an antibody to a shear-induced expression of a new surface marker (e.g., GP 2b/3a) or of a released internal material (e.g., serotonin or ADP).

In some embodiments, the PAS comprises use of acetylated prothrombin, e.g., as described in Jesty and Bluestein, Anal. Biochem. 272(1): 64-70 and WO2001005948, which are incorporated herein by reference. Platelet assay methods using other well-known assay systems, such as ELISA, radioimmunoassay (RIA) and Western blot analysis have been described in Berman et al., Methods in Enzymology 169:314, 1989, incorporated herein by reference. See also U.S. Pat. No. 5,457,028, incorporated herein by reference.

In some embodiments, the microfluidic device comprises a detection means to measure PAS, e.g., a colorimetric assays or ELISA. Thus, in some embodiments, the technology provides for the measurement of anti-thrombotic drug efficacy under device-specific and patient specific conditions, allowing tailoring of individual drug therapies and thus will significantly improve patient safety and long term outcomes.

In some embodiments of the technology provided herein, microfabrication techniques are used to produce a microfluidic device. For example, in some embodiments a microfluidic device is produced by a method comprising replica molding using soft lithography methods. In some embodiments, replica molding using soft lithography comprises producing microfluidic platforms from polydimethylsiloxane (PDMS). PDMS is a silicon rubber that provides advantages related to fabrication, physical properties, and economy (see, e.g., J. Friend and L. Yeo. "Fabrication of microfluidic devices using polydimethylsiloxane," Biomicrofluidics, vol. 4, pp: 026502, 2010). PDMS microfluidic platforms have further advantages related to transparency, gas permeability, and chemical stability (e.g., chemical inertness).

In various embodiments, microfluidic devices are fabricated from various materials using techniques such as laser stenciling, embossing, stamping, injection molding, masking, etching, and three-dimensional soft lithography. Laminated microfluidic devices are further fabricated with adhesive interlayers or by thermal adhesiveless bonding techniques, such as by pressure treatment of oriented polypropylene. The microarchitecture of laminated and molded microfluidic devices can differ.

In some embodiments, microchannels are constructed of layers formed by extrusion molding. The flow characteristics of microchannels are significant because of the surface effects in the microflow regime. Surface tension and viscosity influence (e.g., enhance) surface roughness effects. In some embodiments, the narrowest dimension of a channel has the most profound effect on flow. Flow in channels that have rectangular or circular cross-sectional profiles is controlled by the diagonal width or diameter; thus, in some embodiments, channel design is typically varied to take advantage of this behavior. In some embodiments, reduction of taper in the direction of flow leads to a wicking effect for diameters below 200 micrometers. Conversely, flow can be stopped by opening a channel to form a bulb; then, flow can be restored by applying a pressure. Vias in a channel can be designed to promote directional flow, e.g., to provide a type of solid-state check valve.

In some embodiments, microfluidic devices described herein are fabricated from an elastomeric polymer such as, e.g., polyisoprene, polybutadiene, polychlorophene, polyisobutylene, poly(styrene-butadiene-styrene), nitriles, polyurethanes, or polysilicones. In some embodiments, GE RTV 615, a vinyl-silane crosslinked (type) silicone elastomer (family) or polydimethysiloxane (PDMS) (e.g., sold as HT-6135 and HT-6240 from Bisco Silicons, Elk Grove, Ill.) is useful. The choice of materials typically depends upon the particular material properties (e.g., solvent resistance, stiffness, gas permeability, and/or temperature stability) required for the application being conducted. In some embodiments, elastomeric materials that are used in the manufacture of components of the microfluidic devices are described in Unger (2000) Science 288:113-116, incorporated herein by reference in its entirety. Some elastomers of the present devices are used as diaphragms. In some embodiments, elastomers are selected for their porosity, impermeability, chemical resistance, wetting, and passivating characteristics in addition to their stretch and relax properties. In some embodiments, an elastomer is selected for its thermal conductivity. For example, Micrometrics Parker Chomerics Therm A Gap material 61-02-0404-F574 (0.020" thick) is a soft elastomer (<5 Shore A) needing only a pressure of 5 to 10 psi to provide a thermal conductivity of 1.6 W/m-K.

Computational Fluid Dynamics Analysis

In some embodiments, computational fluid dynamics (CFD) is used to characterize fluid flow through a device. In particular, CFD uses numerical methods and algorithms to solve and analyze problems that involve fluid flows, e.g., to simulate the interaction of liquids and gases with surfaces defined by boundary conditions. In some embodiments comprising use of CFD, a probability density function (PDF) method is used (see, e.g., Lundgren (1969). "Model equation for nonhomogeneous turbulence" Physics of Fluids A 12 (3): 485-497). In particular, PDF methods describe fluid flows in terms of the aggregate properties of a collection of modeled particles using probability functions describing the probability that a fluid has a velocity between v and v+dv at a point location x in the modeled system. See, e.g., Ferziger and Peric, *Computational Methods for Fluid Dynamics*, Springer (1999), incorporated herein by reference.

In some embodiments, a two-step CFD simulation is performed comprising: 1) a steady flow simulation with a constant flow rate; and 2) a subsequent transient two-phase flow simulation in which a discrete particulate phase (e.g., platelets) is modeled to flow through a microchannel. In some embodiments, the fluid is modeled in one or both steps as incompressible and newtonian; and having a density of 1000 to 1200 kg/m$^3$ and a dynamic viscosity of approximately 3 to 4 cP, which is similar to whole blood at 37° C. In the CFD analysis, some embodiments modeled a microfluidic device using a discretized mapping scheme comprising 380,000 hexahedral elements. In some embodiments, blood is modeled as a two-phase system comprising neutrally buoyant particles that are solid spheres of approximately 3-μm diameter. In some embodiments, a computer performing the instructions of a CFD software package (e.g., a commercial finite volume solver such as ANSYS FLUENT (Ansys Inc., USA)) is used to perform the analyses.

Samples and Sample Handling

The technology relates to the processing of samples, e.g., biological samples. Examples of samples include various fluid samples. In some instances, the sample is a bodily fluid sample from the subject. In some embodiments, the sample is an aqueous or a gaseous sample. In some embodiments, the sample includes one or more fluid component. In some embodiments, solid or semi-solid samples are provided. In some embodiments, the sample comprises tissue collected from a subject. In some embodiments, the sample comprises a bodily fluid, secretion, and/or tissue of a subject. In some embodiments, the sample is a biological sample. In some embodiments, the biological sample is a bodily fluid, a secretion, and/or a tissue sample. Examples of biological samples include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, micropiota, meconium, breast milk, and/or other excretions. In some embodiments, the sample is provided from a human or an animal, e.g., in some embodiments the sample is provided from a mammal (e.g., a vertebrate) such as a murine, simian, human, farm animal, sport animal, or pet. In some embodiments, the sample is collected from a living subject and in some embodiments the sample is collected from a dead subject.

In some embodiments, the sample is collected fresh from a subject and in some embodiments the sample has undergone some form of pre-processing, storage, or transport.

In some embodiments, the sample is provided to a microfluidic device from a subject without undergoing intervention or much elapsed time. In some embodiments, the subject contacts the microfluidic device to provide the sample.

In some embodiments, a subject provides a sample and/or the sample may be collected from a subject. In some embodiments, the subject is a patient, clinical subject, or pre-clinical subject. In some embodiments, the subject is undergoing diagnosis, treatment, and/or disease management or lifestyle or preventative care. The subject may or may not be under the care of a health care professional.

In some embodiments, the sample is collected from the subject by puncturing the skin of the subject or without puncturing the skin of the subject. In some embodiments, the sample is collected through an orifice of the subject. In some embodiments, a tissue sample (e.g., an internal or an external tissue sample) is collected from the subject. In some embodiments, the sample is collected from a portion of the subject including, but not limited to, the subject's finger, hand, arm, shoulder, torso, abdomen, leg, foot, neck, ear, or head.

In some embodiments, one type of sample is accepted and/or processed by the microfluidic device. Alternatively, in some embodiments multiple types of samples are accepted and/or processed by the microfluidic device. For example, in some embodiments the microfluidic device is capable of accepting one or more, two or more, three or more, four or more, five or more, six or more, seven or more, eight or more, nine or more, ten or more, twelve or more, fifteen or more, twenty or more, thirty or more, fifty or more, or one hundred or more types of samples. In some embodiments, the microfluidic device is capable of accepting and/or processing any of these numbers of sample types simultaneously and/or at different times from different or the same matrices. For example, in some embodiments the microfluidic device is capable of preparing, assaying, and/or detecting one or multiple types of samples.

The technology is not limited in the volume of sample that is processed by the microfluidic device. Accordingly, embodiments provide that any volume of sample is provided from the subject or from another source. Examples of volumes may include, but are not limited to, approximately 10 mL or less, 5 mL or less, 3 mL or less, 1 mL or less, 500 µL or less, 300 µL or less, 250 µL or less, 200 µL or less, 170 µL or less, 150 µL or less, 125 µL or less, 100 µL or less, 75 µL or less, 50 µL or less, 25 µL or less, 20 µL or less, 15 µL or less, 10 µL or less, 5 µL or less, 3 µL or less, 1 µL or less, 500 nL or less, 250 nL or less, 100 nL or less, 50 nL or less, 20 nL or less, 10 nL or less, 5 nL or less, 1 nL or less, 500 pL or less, 100 pL or less, 50 pL or less, or 1 pL or less. The amount of sample may be approximately a drop of a sample. The amount of sample may be approximately 1 to 5 drops of sample, 1 to 3 drops of sample, 1 to 2 drops of sample, or less than a drop of sample. The amount of sample may be the amount collected from a pricked finger or fingerstick. Any volume, including those described herein, is provided to the device in various embodiments.

Further, in some embodiments a sample collection unit and/or sample reaction chamber is integral to the microfluidic device. And, in some embodiments the sample collection unit and/or sample reaction chamber is separate from the microfluidic device. In some embodiments, the sample collection unit and/or sample reaction chamber is removable and/or insertable from the microfluidic device or is removable and/or insertable from an apparatus comprising the microfluidic device. In some embodiments, the sample collection unit and/or sample reaction chamber is provided in the microfluidic device; in some embodiments the sample collection unit and/or sample reaction chamber is not provided in the microfluidic device. In some embodiments, the microfluidic device is removable and/or insertable from an apparatus.

In some embodiments a sample collection unit and/or sample reaction chamber is configured to receive a sample. In some embodiments, the sample collection unit is capable of containing and/or confining the sample. In some embodiments, the sample collection unit is capable of conveying the sample to other components, modules, and chambers of the microfluidic device.

In some embodiments, a microfluidic device is configured to accept a single sample; in some embodiments a microfluidic device is configured to accept multiple samples. In some embodiments, the multiple samples comprise multiple types of samples. For example, in some embodiments a single microfluidic device handles a single sample at a time. For example, in some embodiments a microfluidic device receives a single sample and performs one or more sample processing steps, such as a lysis steps, isolation steps, reaction steps, and/or a separation steps with the sample. In some embodiments, the microfluidic device completes processing a sample before accepting a new sample.

In other embodiments, a microfluidic device is capable of handling multiple samples simultaneously. In one example, a microfluidic device receives multiple samples simultaneously. In some embodiments, the multiple samples comprise multiple types of samples. Alternatively, in some embodiments the microfluidic device receives samples in sequence. Samples are provided in some embodiments to the microfluidic device one after another or, in some embodiments, samples are provided to the microfluidic device after any amount of time has passed. A microfluidic device in some embodiments begins sample processing on a first sample, receives a second sample during said sample processing, and processes the second sample in parallel with the first sample. In some embodiments, the first and second samples are not the same type of sample. In some embodiments, the microfluidic device processes any number of samples in parallel, including but not limited to more than and/or equal to approximately one sample, two samples, three samples, four samples, five samples, six samples, seven samples, eight samples, nine samples, ten samples, eleven samples, twelve samples, thirteen samples, fourteen samples, fifteen samples, sixteen samples, seventeen samples, eighteen samples, nineteen samples, twenty samples, twenty-five samples, thirty samples, forty samples, fifty samples, seventy samples, one hundred samples.

In some embodiments, the microfluidic device processes one, two, or more samples in parallel. The number of samples that are processed in parallel may be determined by the number of available modules, reaction chambers, and/or components in the microfluidic device.

When a plurality of samples is processed simultaneously, embodiments provide that the samples begin and/or end processing at any time. For example, the samples need not begin and/or end processing at the same time. In some embodiments, a first sample has completed processing while a second sample is still being processed. In some embodiments, the second sample has begun processing after the first sample has begun processing. As samples have completed processing, additional samples are added to the device in some embodiments. In some embodiments, the microfluidic device runs continuously with samples being added to the device as various samples have completed processing.

In some embodiments, multiple samples are provided simultaneously. In some embodiments, multiple samples are not the same type of sample. In some embodiments, multiple sample collection units are provided to a microfluidic device. In some embodiments, the multiple sample collection units receive samples simultaneously and in some embodiments the multiple sample collection units receive samples at different times. In some embodiments, multiples of any of the sample collection mechanisms described herein are used in combination.

In some embodiments, multiple samples are provided in sequence. In some embodiments, multiple sample collection units are used and in some embodiments single sample collection units are used. Embodiments provide any combination of sample collection mechanisms described herein. In some embodiments, a microfluidic device accepts one sample at a time, two samples at a time, or more. In some embodiments, samples are provided to the microfluidic device after any amount of time has elapsed.

Testing

In some embodiments, a subject is tested to assess thrombogenic risk by testing a blood sample from the patient to determine if a drug is mitigating the thrombogenic risk. In some embodiments, a patient is tested for thrombogenic risk, treated with an anti-thrombogenic drug, and then tested again for thrombogenic risk to monitor the response to anti-thrombogenic therapy. In some embodiments, cycles of testing and treatment occur without limitation to the pattern of testing and treating (e.g., test/treat, test/treat/test, test/treat/test/treat, test/treat/test/treat/test, test/treat/treat/test/treat/treat, etc), the periodicity, or the duration of the interval between each testing and treatment phase.

Computer and Software

In some embodiments, the technology described herein is associated with a programmable machine designed to perform a sequence of arithmetic or logical operations, e.g., as provided by the methods described herein, either contiguous to the microfluidic device, proximate, or utilized in concert. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a processor or a microprocessor) for executing a series of instructions (e.g., a method as provided herein) to read, manipulate, and store data. Some embodiments comprise one or more processors. In some embodiments, a processor provides instructions to control one or more valves, components, modules, thermoelectric components, piezoelectric components, pumps, reagent supplies, etc. in the microfluidic device and/or apparatus.

In some embodiments, a microprocessor is part of a system comprising one or more of a CPU, a graphics card, a user interface (e.g., comprising an output device such as a display and an input device such as a keyboard), a storage medium, and memory components. Memory components (e.g., volatile and/or nonvolatile memory) find use in storing instructions (e.g., an embodiment of a process as provided herein) and/or data. Programmable machines associated with the technology comprise conventional extant technologies and technologies in development or yet to be developed (e.g., a quantum computer, a chemical computer, a DNA computer, an optical computer, a spintronics based computer, etc.). Some embodiments provide a computer that includes a computer-readable medium.

The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor, such as the processor of client, with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, Swift, Ruby, Unix, and JavaScript.

Computers are connected in some embodiments to a network or, in some embodiments, can be stand-alone machines. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computer-related to aspects of the technology provided herein may be any type of processor-based platform that operates on any operating system, such as Microsoft Windows, Linux, UNIX, Mac OS X, etc., capable of supporting one or more programs comprising the technology provided herein. All such components, computers, and systems described herein as associated with the technology may be logical or virtual.

Data Collection and Analysis

In some embodiments, assay data are produced. Following the production of assay data, the assay data are reported to a data analysis operation in some embodiments. Data may be stored on the device, telemetered to a proximate data storage means or at a distance via bluetooth or other contained transmission means or via connectivity to the worldwide web. To facilitate data analysis in some embodiments, the assay data are analyzed by a digital computer. In some embodiments, the computer is appropriately programmed for receipt and storage of the assay data and for analysis and reporting of the assay data gathered, e.g., to provide a drug dosage, shear stress profile, or thrombogenicity in a human or machine readable format.

In some embodiments, a computer-based analysis program is used to translate the data generated by an assay (e.g., the presence, absence, or amount of a given marker or markers of thrombogenic state and/or platelet activation) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to utilize the information immediately to optimize the care of the subject. The present invention contemplates any method capable of receiving, processing, and transmitting the information to and from laboratories conducting the assays, information providers, medical personal, and subjects.

EXAMPLES

Example 1—Steady Flow Simulation

During the development of embodiments of the technology provided herein, experiments were conducted to model a VAD using a steady flow simulation. In particular, the model was constructed using a constant uniform velocity of 2.7 cm/s (corresponding to a flow rate of 2 μl/min) at the inlet of the fluid domain and a zero pressure at the outlet. At the assigned flow rate, the maximum Reynolds number (<1) was substantially below the transition flow regime. A SIMPLE method was used for pressure-velocity coupling and a second order upwind scheme was chosen for the discretization of momentum equation. The simulation was run until stabilization of the solution (e.g., a difference lower than 1% in the velocity and pressure fields between two consecutive iterations was considered acceptable). A grid sensitivity analysis was performed on three different grids with 200,000 (coarse), 380,000 (intermediate), and 720,000 (fine) elements. Differences in terms of velocity distributions, pressure gradients across the stress generating features, and wall shear stress values were compared and were found to be lower than 5% between the coarse and the intermediate grid, and lower than 2% between the intermediate and the fine grid. Hence, the results of the intermediate grid were considered mesh-independent and this grid was used for the analyses.

Example 2—Transient Two-Phase Flow Simulations

During the development of embodiments of the technology provided herein, platelet trajectories within the microchannels were modeled and characterized as described in Pelosi et al. (2014) "Computational evaluation of the thrombogenic potential of a hollow-fiber oxygenator with integrated heat exchanger during extracorporeal circulation" Biomechanics and Modeling in Mechanobiology 13(2): 349-361, incorporated herein by reference. In short, the method uses a multiscale Lagrangian to determine the trajectory and stress loading history experienced by platelets. The stress loading history is incorporated into a damage accumulation model to estimate the platelet activation state (PAS) associated with repeated passes of the blood within a device.

Once convergence of the steady flow simulation was reached, a transient simulation was performed in which a discrete particulate phase representing platelets was injected from the inlet of the channel. The DPM model implemented in ANSYS Fluent® was used to model and solve the discrete phase. The particles were assumed as inert, buoyant, and spherical, with characteristics similar to human platelets (e.g., a diameter of 3 μm and the density of water (998 kg/m$^3$). The solver computes the trajectory of each particle by solving its momentum equation in a lagrangian reference frame:

$$d\vec{u}_p/dt = F_D(\vec{u}_p - \vec{u}) + g(\rho_p - \rho)/\rho_p \quad (1)$$

where $u_p$ and $\rho_p$ are the velocity and density of the particle, u and ρ are the velocity and density of the continuous phase, and $F_d$ is a drag coefficient that depends on the particle shape, dimension, and velocity; and on the velocity and viscosity of the continuous phase. The discretization step for the advancement in time of the solution was set to 0.1 ms and the simulation was run until all the particles escaped the fluid domain. A fully-coupled approach was used, thus accounting for the interaction between the discrete and the continuous (e.g., fluid) phase. At each time step, both the phases were solved alternatively until convergence. At each time step, the scalar stress (σ) along each platelet trajectory was computed from the components of the fluid stress tensor in the current platelet position. For each trajectory, the linear stress accumulation (SA) was computed by integrating the instantaneous product of the scalar stress and the exposure time to it. In this way, a stochastic distribution of SA for multiple platelet trajectories within the microfluidic model was obtained. This distribution was then used to construct the probability distribution function (PDF) of the multiple SAs, which represents the flow-induced thrombogenic potential of the device. The SA distribution for the VAD (e.g., HMII) microfluidic model was compared to previous data describing the shear-related thrombogenic potential of the actual VAD (see, e.g., W. Chiu, G. Girdhar, M. Xenos, Y. Alemu, J. S. Soares, S. Einav, M. Slepian, and D. Bluestein, "Thromboresistance comparison of the Heart-MateII Ventricular Assist Device With the Device Thrombogenicity Emulation-Optimized HeartAssist 5 VAD," Journal of Biomechanical Engineering, vol. 136, pp. 021014, 2014).

Example 3—Results

Figure 2:
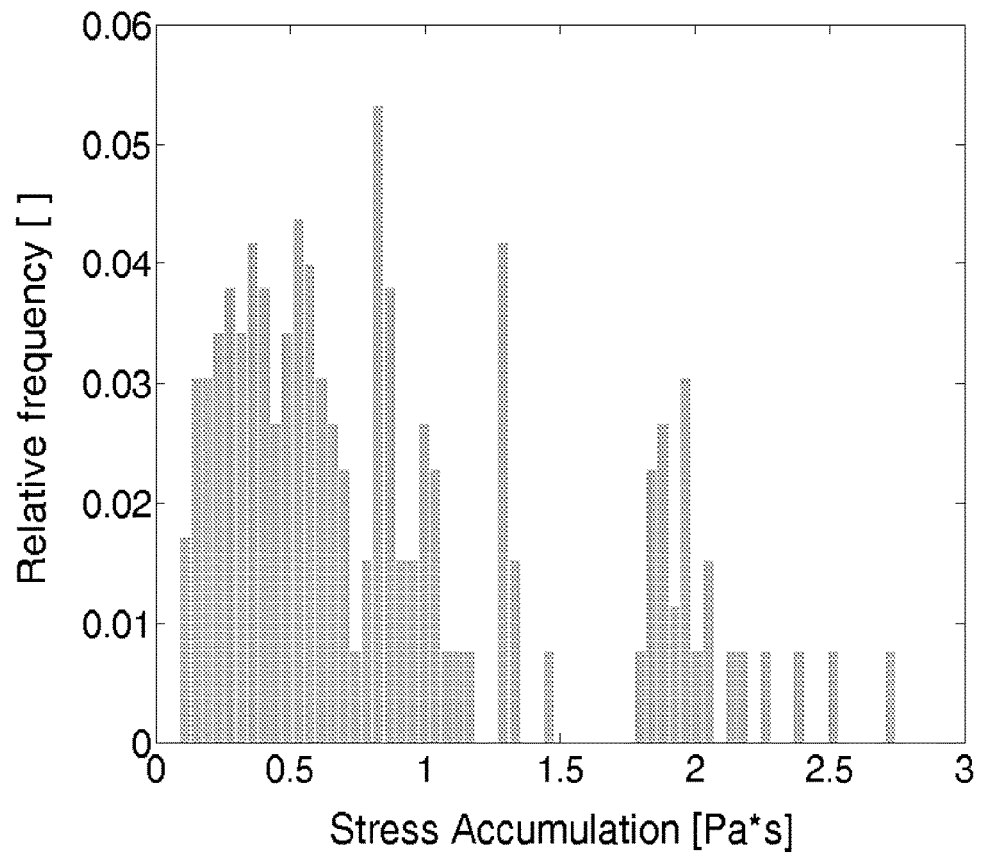
FIG. 2 is a plot showing the PDF of SA obtained in the microfluidic simulation of a HMII VAD.

During the development of embodiments of the technology described herein, experiments were conducted to model the linear stress accumulation (SA) of a VAD (e.g., a HMII device). Data collected during the experiments were used to calculate the PDF of SA in a microfluidic simulation of the HMII VAD (see FIG. 2). Analysis of the data indicates that the PDF is similar to data computed from the macroscale simulation of the device (see, e.g., Nobili, M., Sheriff, J., Morbiducci, U., Redaelli, A., & Bluestein, D. "Platelet activation due to hemodynamic shear stresses: damage accumulation model and comparison to in vitro measurements." ASAIO Journal, 54(1), pp. 64-72, 2008) (see Table 1). In Table 1, the 10th, 50th and 90th percentiles of the PDFs of SA are reported.

TABLE 1

SA distributions of the real HMII VAD and simulated microfluidic model

| | SA percentile distribution [Pa-s] | | |
|---|---|---|---|
| | 10$^{th}$ | 50$^{th}$ | 90$^{th}$ |
| HMII_microfluidic | 0.3 | 0.9 | 2.7 |
| HMII VAD | 0.3 | 0.8 | 2.9 |

Figure 3:
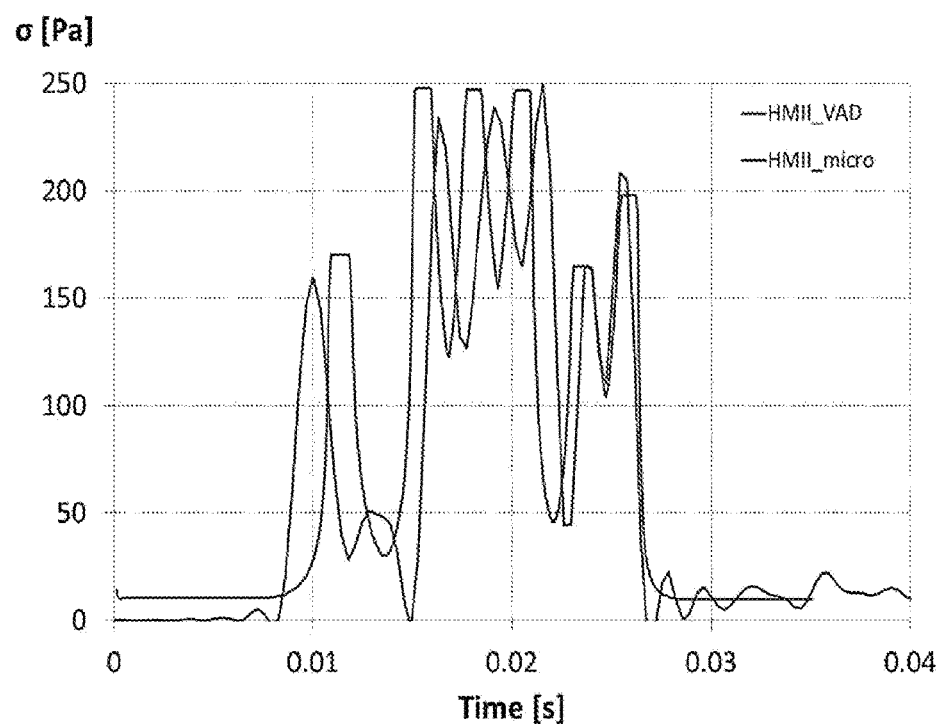
FIG. 3 is a plot comparing the scalar stress curves in the simulated HMII microfluidic device and in the macroscale HMII VAD.

The data also indicated a good correlation of scalar stress waveforms (see in FIG. 3). In particular, the data indicated similar scalar stress curves for the 90th percentile of SA obtained in HMII microfluidic simulation and the corresponding waveform of the macroscale VAD model (FIG. 3). The total pressure drop in the microfluidic model was 0.7 atm.

Example IV

Figure 4A:
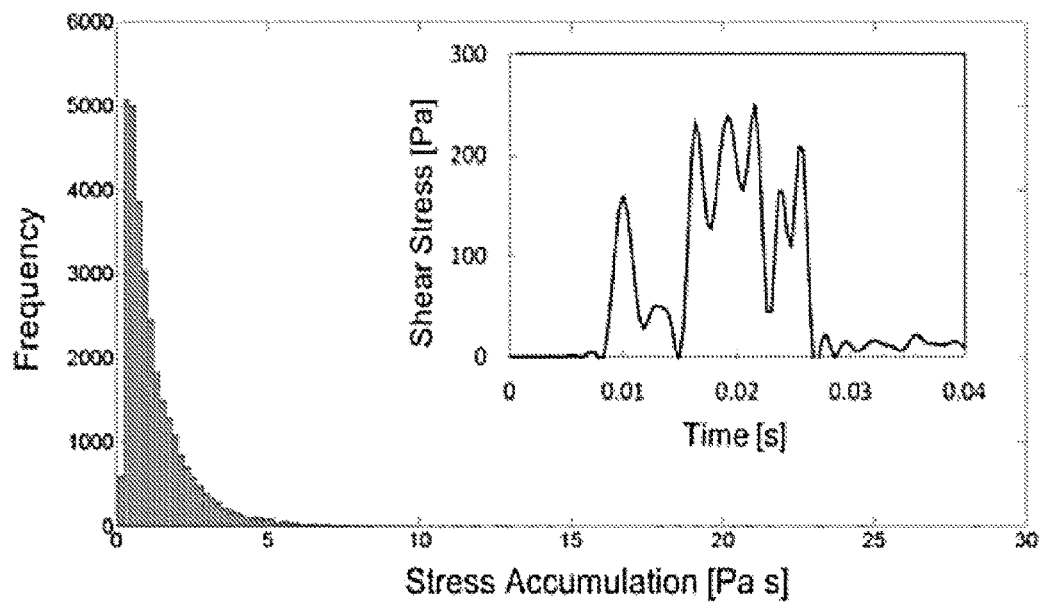
FIG. 4: PDF of the SA of HeartAssist5 (a) and HeartMateII (b) VADs and representative shear stress waveforms extracted from the 90th percentile of their PDFs (Chiu et al. 2014 J. Biomech. Eng. 136:021014).
Figure 4B:
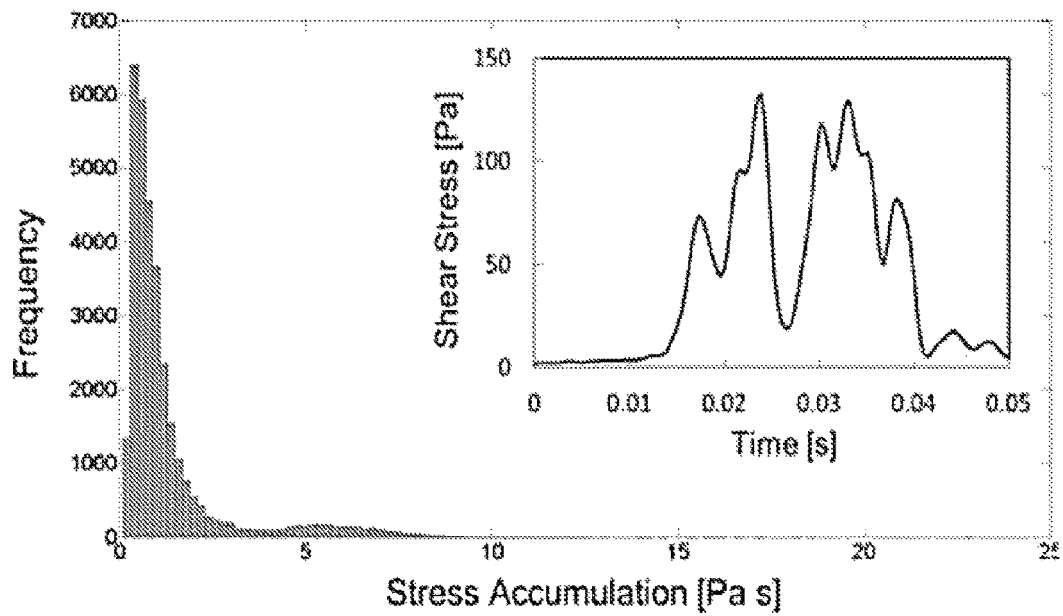

This experiment describes the modulation of the geometry of microfluidic channels in order to generate shear stress history patterns that replicate MCS device shear patterns. In particular, two commercial VADs, the HeartAssist5 (HA5, MicroMed Technology Inc., Houston, Tex., USA) and HeartMateII (HMII, Thoratec Corportation, Pleasanton, Calif., USA) VADs, were studied. Their PDFs and hotspot shear stress waveforms (Chiu et al. 2014 J. Biomech. Eng. 136:021014) are shown in FIG. 4.

The shear stress waveforms of the two VADs were characterized by the superimposition of stress peaks ranging from 60 to 250 Pa, for an overall duration of 10-20 ms (with durations of each peak varying from 3 to 6 ms). These data were the starting point for the design of the microfluidic platforms.

Microfluidic Model Design
Design of Microfluidic Stress-Generating Templates

As a first step, a sample shear stress waveform with a triangular shape was considered, featuring a baseline shear stress value lower than 20 Pa, a peak shear stress of 130 Pa and duration of 4 ms. This sample waveform was chosen as a template pattern, characterized by typical values of shear stress and exposure time observed in MCS devices. The goal of this step was to test the feasibility of using microfluidic devices to replicate typical features of shear stress waveforms experienced by blood platelets in actual MCS devices.

Figure 5A:
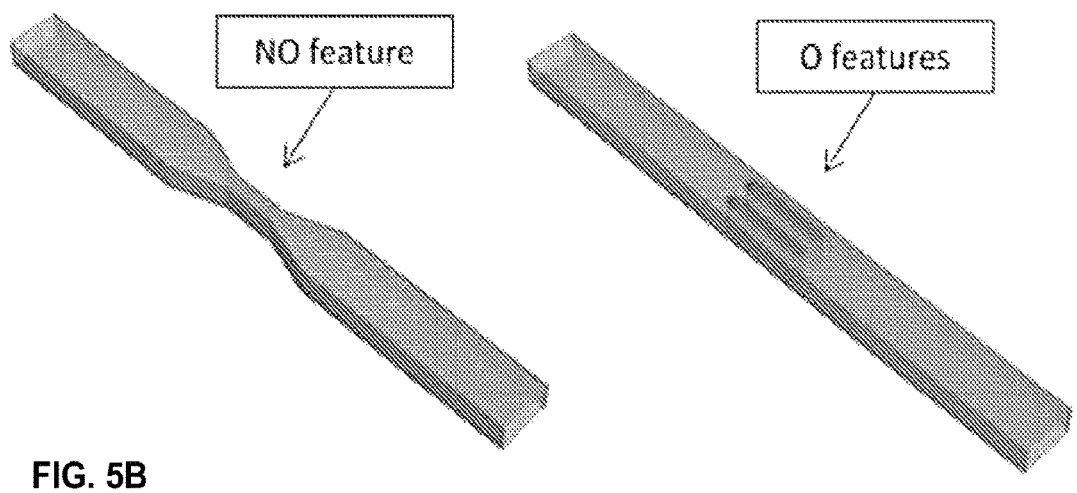
FIG. 5: A) Example of non-obstructive (left) and obstructive (right) geometries. B) Geometries investigated in 2.1.2. Subpanels show the enlarged view of the three different kinds of narrowing: i) angled, ii) sharp and sudden, and iii) smoothed.

To this end, two microfluidic layout configurations were designed at different scale-sizes, corresponding to the opposing limits of attainable geometries with standard photo-lithography: a first configuration (M1) with a rectangular reference channel cross-section of 50 μm×25 μm (width×height) and a second configuration (M2) with a reference channel cross-section of 500 μm×200 μm (width×height). As in most microfluidic applications, the heights of features in each configuration were maintained constant, achieving the desired levels of shear stress by either modulating the width of the channel (non-obstructive, NO, FIG. 5a) or inserting obstacles along the channel (obstructive, O, FIG. 5a). In both cases, the peak shear stress was obtained by decreasing the flow area with respect to the reference section of the channel.

For the M1 configuration, the obstructive model (M1_O2) was obtained by inserting two oval-shape obstacles along the channel, while for the M2 configuration, either one and three obstacles were designed (obtaining M2_O1 and M2_O3 models). The dimensions of the obstacles were determined in order to obtain the same peak shear stress values as in the corresponding NO geometry, at the same flow rate. The dimensions of the designed models are summarized in Table 2.

TABLE 2

Dimensions of the models designed in 2.1.1: width (W) of the reference cross-section, height (h) and length (L) of the channel; width ($W_{feat}$) and length ($L_{feat}$) of the stress-generating features. $W_{feat}$ refers to the width of the narrowed section in NO models and to the width of each obstacle in O models.

|  | M1_NO | M1_O2 | M2_NO | M2_O1 | M2_O3 |
|---|---|---|---|---|---|
| N. of obstacles | — | 2 | — | 1 | 3 |
| W (μm) | 50 | 50 | 500 | 500 | 500 |
| h (μm) | 25 | 25 | 200 | 200 | 200 |
| L (μm) | 700 | 535 | 4940 | 4200 | 3930 |
| $W_{feat}$ (μm) | 15 | 13 | 120 | 332 | 94 |
| $L_{feat}$ (atm) | 300 | 390 | 1940 | 4200 | 2100 |

Achieving Different Shear Stress Levels

As a second step of the approach, how the levels and waveforms of shear stress in the microfluidic devices can be modulated was tested by varying the shapes and dimensions of the shear stress-generating features.

Figure 5B:
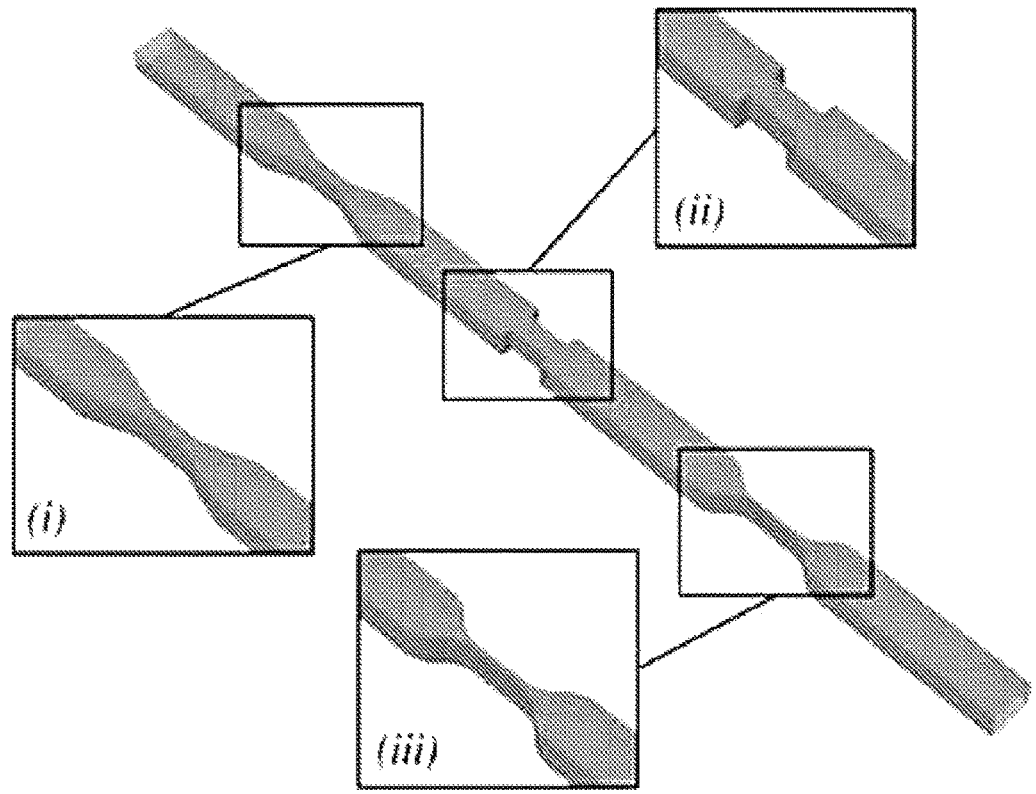

To this end, a further NO model was designed, characterized by 3 different NO stress-generating features (M1_3 SGF) as shown in FIG. 5b: the NO feature described in the first designing step (subpanel i), an abrupt contraction followed by a sudden expansion (subpanel ii), and a smoothed narrowing feature without sharp corners (subpanel iii). The features were sized in order to generate shear stress peaks differing by three orders of magnitude (160, 80 and 1000 Pa, respectively).

Design of Microfluidic Devices to Replicate Commercial VADs

Figure 6A:
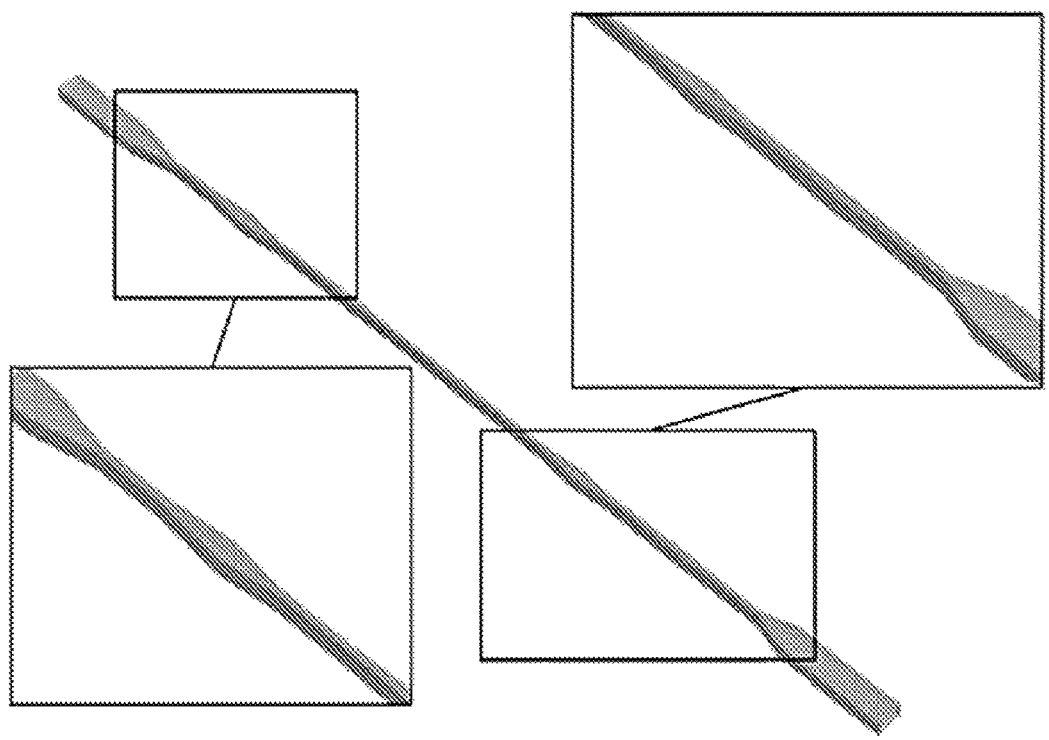
FIG. 6: Microfluidic units emulating the shear stress waveforms corresponding to the $90^{th}$ percentile of SA of HMII (a) and HA5 (b) VADs with enlarged views of the channel features.
Figure 6B:
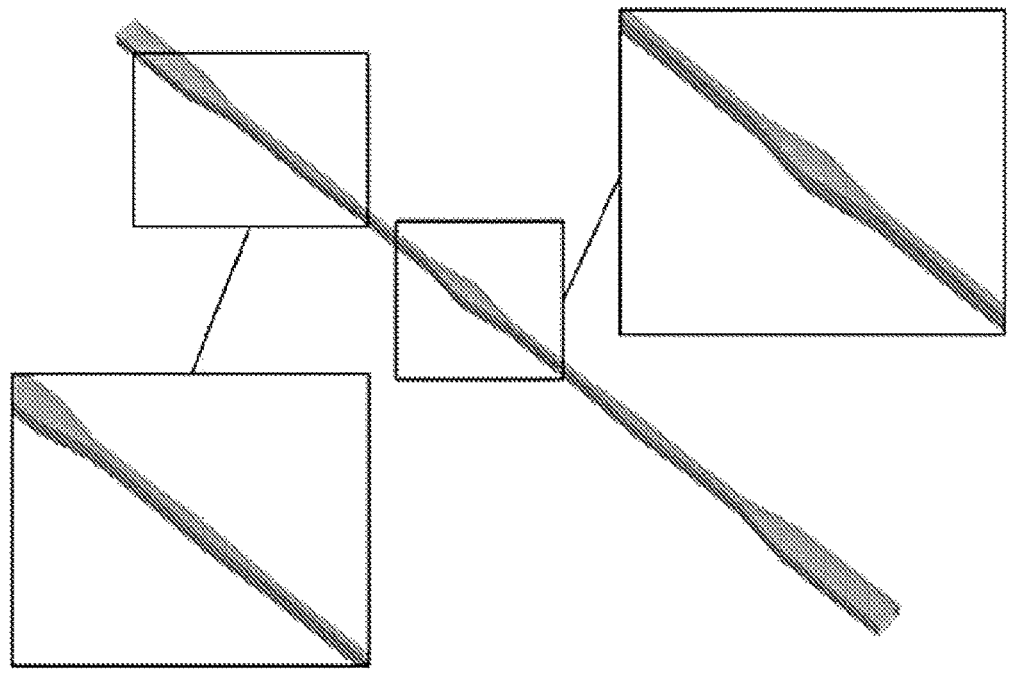

Finally, two commercial VADs were considered: the HMII and the HA5 axial flow pumps. These devices have recently been studied through CFD analyses by Chiu and colleagues (Chiu et al. 2014 J. Biomech. Eng. 136:021014), who used a discrete phase model to extract shear stress waveforms along platelet trajectories. Here, two microfluidic devices, termed the HMII microfluidic and the HA5 microfluidic (FIG. 6), were designed in order to replicate the critical shear stress waveforms extracted by Chiu and colleagues (corresponding to the 90th percentile of the stress accumulation distribution of each VAD). The original shear stress waveforms were described as a series of triangular shaped shear stress patterns, that were replicated by a corresponding series of stress-generating features in the emulating microchannels. A reference channel cross-section of 50 μm×25 μm and a NO configuration was chosen in both cases.

Computational Fluid Dynamic Analyses

The flow fields in all the described microdevices were analyzed through CFD using the commercial finite volume solver ANSYS Fluent® (Ansys Inc., USA) (Pelosi Model Mechanobiol. 13:349-361 (2014)). NO models were discretized with hexaedral elements using a mapping scheme, while the obstructive models and M1_3 SGF model were discretized with tetrahedral elements. The fluid phase, representing whole blood, was modeled asincompressible with a density of 1060 Kg/m3. A non-Newtonian power-law model was implemented in Fluent and used to model the rheological properties of blood. In particular, the model proposed by Ballyk and colleagues (1994) Biorheology 31(5):565-586 was adopted, and computed the parameters by fitting published experimental data related to whole blood at 37° C. (Chien et al. 1966 J. Appl. Physiol. 21:81-87). A SIMPLE method was used for pressure-velocity coupling and a second order upwind scheme was chosen for the discretization of the momentum equation. A constant uniform velocity and zero pressure were imposed as boundary conditions at the inlet and the outlet of the fluid domain, respectively. In all the M1 models, and in the two VAD emulating microfluidic models, a velocity of 2.7 cm/s was assigned at the inlet, while in the M2 models, a velocity of 17.3 cm/s was imposed. In all the simulations the maximum Reynolds number was well below the limit of the transition flow regime. The highest Reynolds number was 40, occurring in model M2 NO.

The steady-state velocity and pressure fields were first computed through a steady flow simulation. Once convergence was reached, a transient simulation was run in which a discrete phase, modeled as buoyant spherical particles, was injected from a cross-section downstream of the inlet surface. The discrete phase was assigned characteristics of human platelets, with a diameter of 3 μm and the density of water, 998 Kg/m3. The trajectory of each particle was computed by solving the momentum equation for the particle in a Lagrangian reference frame:

$$\frac{d\vec{u}_p}{dt} = F_D(\vec{u} - \vec{u}_p) + g\frac{\rho_p - \rho}{\rho_p} \quad (1)$$

where $\vec{u}$ and $\vec{u}_p$ refer to the fluid and particle velocity, respectively; $\rho$ and $\rho_p$ to their density; and $F_D$ is a drag coefficient that depends on both the discrete and the continuous phase, and is expressed as $$F_D = \frac{18\mu}{\rho_p d_p^2} \frac{C_D Re_p}{24} \quad (2)$$

where $Re_p$ is the particle Reynolds number, computed as $$Re_p = \frac{\rho_p d_p |\vec{u}_p - \vec{u}|}{\mu} \quad (3)$$

and $C_D$ is a coefficient calculated according to the spherical drag law $$C_D = a_1 + \frac{a_2}{Re} + \frac{a_3}{Re^2} \quad (4)$$

where $a_1$, $a_2$ and $a_3$ are constant values that apply over several ranges of $Re_p$ (Morsi and Alexander 1972 J. Fluid Mech. 55(2):193-208).

The discretization step for the advancement in time of the solution was set to 0.1 ms and for each model the simulation was run until all the particles escaped the fluid domain. A fully coupled approach was used, thus accounting for the mutual influence between discrete and continuous phases: at each time step both phases are solved alternatively until convergence.

According to previous computational studies (Apel et al. 2001 Artif. Organs 25(5):341-347, Alemu and Bluestein 2007 Artif Organs. 31(9):677-88), the so-called scalar stress was computed from the fluid stress tensor $t_{ij}$, as in (5)

$$\sigma = \frac{1}{\sqrt{3}}\sqrt{\tau_{11}^2 + \tau_{22}^2 + \tau_{33}^2 - \tau_{11}\tau_{22} - \tau_{11}\tau_{33} - \tau_{22}\tau_{33} + 3(\tau_{12}^2 + \tau_{13}^2 + \tau_{23}^2)} \quad (5)$$

Particle trajectories were extracted from the discrete phase simulations. Moreover, the scalar stress along each trajectory and at each time step was also exported: from each simulated model, N scalar stress waveforms were obtained (where N is the number of simulated particles in the domain). The linear stress accumulation (SA) of each trajectory was computed as $$SA = \int_0^T \sigma(s)ds \quad (6)$$

thus obtaining a stochastic distribution of SA in each microfluidic model. Indeed, the probability density function (PDF) of SA in a device can be seen as the synthetic description of its flow related thrombogenic potential, thus providing an overall term of comparison with MCS devices.

Results

Design of Microfluidic Stress-Generating Templates

Figure 7:
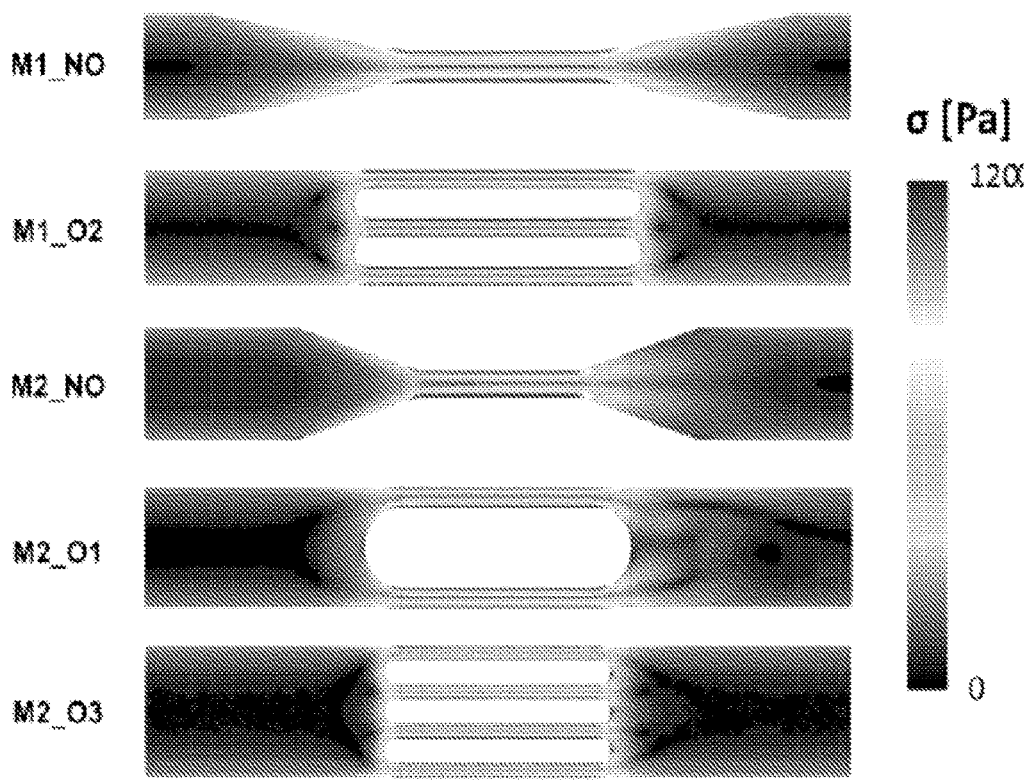
FIG. 7: Contours of scalar stress in the mean longitudinal plane of the stress generating features in the models designed in 2.1.1.

In FIG. 7, the contours of the scalar stress in the mean longitudinal plane of the models designed in the first designing step are shown. The scalar stress levels were similar with maximum scalar stress values ranging from 158 (model M1_NO) to 163 Pa (model M1_O1). This result demonstrated the possibility of achieving similar scalar stress within microfluidic devices by means of stress-generating features differing in kind and dimension. In M2 NO model, flow trails could be observed downstream of the stress-generating feature, unlike model M1 NO, where a symmetric stress distribution was obtained across the stress-generating feature. The latter was characterized by a Stokes flow and the narrowing of the channel did not lead to any flow disturbances. On the contrary, the flow regime was different for configuration M2NO, where the flow rate was 500 fold higher than in M1_NO.

In Table 3, the maximum scalar stress in the fluid domain and the total pressure drop across the channels are reported. Moreover, the distributions of peak scalar stress along particle trajectories and the PDF of SA are reported, both expressed as 10th, 50th and 90th percentile values.

TABLE 3

Maximum scalar stress ($\sigma_{max}$), pressure drop level ($\Delta P$), 10th, 50th and 90th percentiles of $\sigma_{peak}$ along particle trajectories and of SA.

|  | M1_NO | M1_O2 | M2_NO | M2_O1 | M2_O3 |
|---|---|---|---|---|---|
| $\sigma_{max}$ (Pa) | 158 | 162 | 159 | 163 | 1.64 |
| $\Delta P$ (atm) | 0.04 | 0.07 | 0.04 | 0.07 | 0.08 |
| $10^{th}$ percentile of $\sigma_{peak}$ (Pa) | 27 | 32 | 30 | 28 | 34 |
| $50^{th}$ percentile of $\sigma_{peak}$ (Pa) | 58 | 57 | 60 | 56 | 57 |
| $90^{th}$ percentile of $\sigma_{peak}$ (Pa) | 101 | 103 | 98 | 97 | 1.07 |
| $10^{th}$ percentile of SA (Pa s) | 0.07 | 0.10 | 0.08 | 0.10 | 0.11 |
| $50^{th}$ percentile of SA (Pa s) | 0.22 | 0.28 | 0.24 | 0.28 | 0.31 |
| $90^{th}$ percentile of SA (Pa s) | 1.00 | 0.98 | 0.91 | 0.97 | 0.91 |

Obstructive models were characterized by slightly higher peak scalar stress values, with corresponding higher pressure drop across the channel. The scalar stress peaks experienced by the particles were similar in terms of 50th and 90th percentile values, with differences below 7%, with the exception of the 10th percentile of peak scalar stress between M1_NO and M1_O2, which reported a 17% of discrepancy. The distribution of the SA was also comparable between the NO and O models and between the M1 and M2 configurations. The models also reported similar values of peak shear stress duration with an average of peak duration of 5 ms and 4 ms in NO and obstructive models, respectively. The desired template shear stress waveform was then achieved both in terms of peak scalar stress (130 Pa) and duration (in the range 3-6 ms), thus demonstrating the potential use of microfluidics in performing HSD-like shear-controlled experiments. Although similar results were obtained with NO and O features, NO channels have the advantage—given the aspect ratios of obstacles considered here—of being easier to accurately fabricate through soft lithography.

Achieving Different Shear Stress Levels

Figure 8:
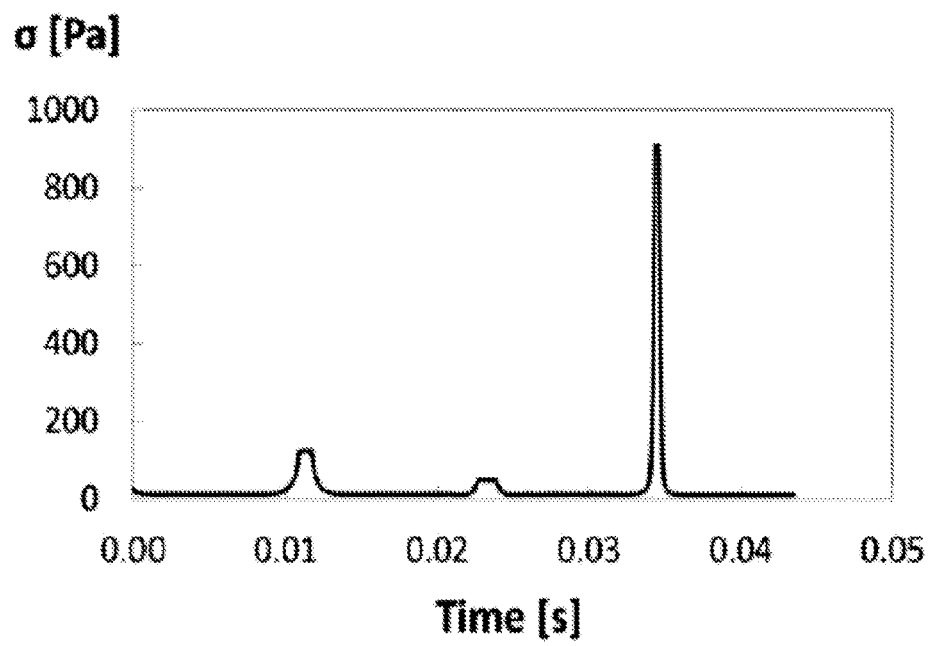
FIG. 8: Scalar stress along a particle flowing in M1_3 SGF, corresponding to the 90th percentile of SA.

The maximum scalar stress levels in the three stress-generating features of M1_3SGF model were 158 Pa, 80 Pa and 1050 Pa, respectively, in accordance with the ranges set in the designing phase. This result demonstrated how it could be possible to span very large ranges of shear stress within a single microfluidic device. The same result could be observed from the transient discrete phase simulation. As an example, the scalar stress along a particle trajectory corresponding to the 90th percentile of SA is shown in FIG. 8.

Microfluidic Devices to Replicate Commercial VADs

As a third step, two microfluidic models (FIG. 6) were designed in order to replicate significant scalar stress trajectories computed in a previous study (Chiu et al. 2014 J. Biomech. Eng. 136:021014) for two commercial VADs: the HMII and the HA5 devices. The PDFs of SA obtained from HMII microfluidic and HA5 microfluidic fitted well with those computed from the macroscale simulations (Chiu et al. 2014 J. Biomech. Eng. 136:021014). In Table 4, the 10th, 50th and 90th percentiles of SA are reported and compared to those of the HMII and HA5 VADs.

TABLE 4

Comparison between SA distributions of the HMII and HA5 VADs (Chiu et al. 2014 J. Biomech. Eng. 136: 021014) and the simulated microfluidic models. The 10th, 50th and 90th percentiles of the PDF of SA are reported.

| | SA percentiles (Pa s) | | |
|---|---|---|---|
| | $10^{th}$ | $50^{th}$ | $90^{th}$ |
| HMII_microfluidic | 0.3 | 0.9 | 2.8 |
| HMII VAD | 0.3 | 0.8 | 2.9 |
| HA5_microfluidic | 0.3 | 0.8 | 2.5 |
| HA5 VAD | 0.4 | 0.9 | 2.7 |

Figure 9A:
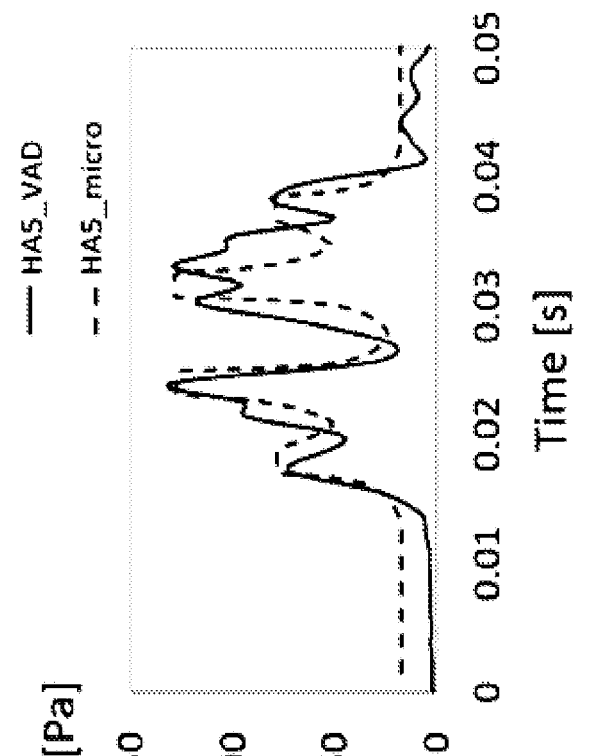
FIG. 9: Comparison between the scalar stress waveforms corresponding to the 90th percentile of SA distribution obtained in the (a) HMII and (b) HA5 VAD simulations at the macroscale (Chiu et al. 2014 J. Biomech. Eng. 136: 021014) and in the corresponding microfluidic simulations.
Figure 9B:
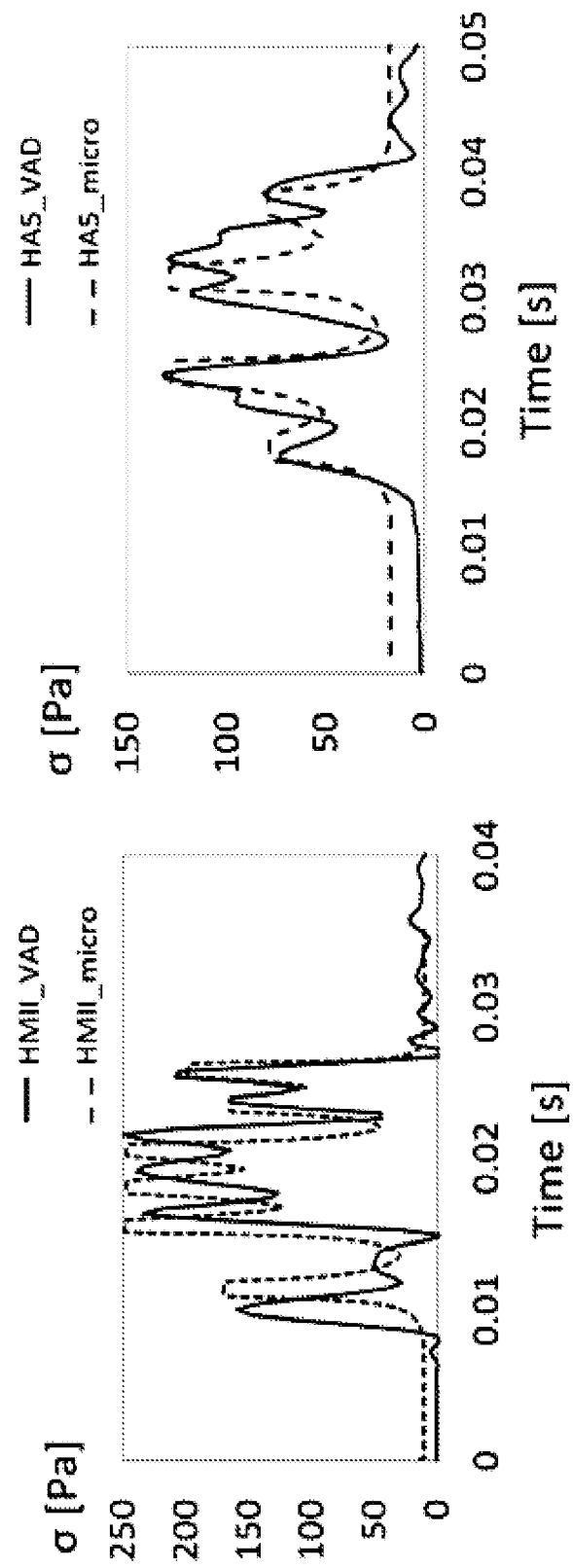

FIG. 9 provides a comparison between the scalar stress waveforms corresponding to the $90^{th}$ percentile of the SAs of the HMII and HA5 VADs and the corresponding simulated microfluidic models. Although schematic, the microfluidic platforms succeeded in capturing the main features of the scalar stress waveforms experienced by blood platelets at the macroscale, in terms of both maximum stress and exposure time. The pressure drop across the two models was 0.7 and 0.6 atm, respectively. If considering experimental constraints in terms of maximum pressure drop (5 atm) across a microfluidic platform, this result means that a single chip could be made of few repetitions of the designed simulated unit.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for monitoring platelet activation state in a subject, the method comprising:
    a) modeling the shear stress profile of a pathology in a medical device,
        wherein the pathology is a cardiovascular pathology,
        wherein the medical device is a mechanical circulatory support device,
        wherein the modeling comprises one or more of device thrombogenicity emulation, producing a probability density function of the medical device, and determining individual particle trajectories for particles flowing through the medical device;
    b) reproducing the shear stress profile of the pathology in the device in a microfluidic device;
    c) flowing a sample from the subject through the microfluidic device, wherein the sample comprises platelets separated from a blood sampled obtained from the subject,
        wherein the sample has a volume of 1 to 100 nanoliters, 1 to 1000 nanoliters, 1 to 100 microliters, or 1 to 1000 microliters; and
    d) testing a platelet activation state of the sample.

2. The method of claim 1 wherein the pathology is a deviation from a normal geometry or flow characteristic.

3. The method of claim 1 wherein the pathology is an arterial narrowing, stenosis, outpouching, anurysm or pseudoaneurysm, dissection, flap, fistula, constriction, thrombus, intinal hyperplasia, or tumor.

4. The method of claim 1 wherein the medical device is a ventricular assist device, stent, total artificial heart, or valve.

5. The method of claim 1 further comprising adjusting the dose of a drug or other therapeutic agent administered to the subject and/or adjusting the dose of an anti-thrombosis drug administered to the subject.

6. The method of claim 1 wherein the sample is acquired from the patient 1 to 10 times a day.

* * * * *